US008692168B2

(12) United States Patent
Benda et al.

(10) Patent No.: US 8,692,168 B2
(45) Date of Patent: Apr. 8, 2014

(54) INFRARED HEATING PANELS, SYSTEMS AND METHODS

(75) Inventors: Steven J. Benda, Cokato, MN (US); Tracy Felder, Winsted, MN (US)

(73) Assignee: TyloHelo Inc., Cokato, MN (US)

( * ) Notice: Subject to any disclaimer, the term of this patent is extended or adjusted under 35 U.S.C. 154(b) by 0 days.

(21) Appl. No.: 12/966,221

(22) Filed: Dec. 13, 2010

(65) Prior Publication Data

US 2011/0315672 A1 Dec. 29, 2011

Related U.S. Application Data

(60) Provisional application No. 61/337,357, filed on Feb. 2, 2010.

(51) Int. Cl.
*F24D 13/02* (2006.01)
*F24D 19/00* (2006.01)
*H05B 3/03* (2006.01)
*H05B 3/06* (2006.01)
*H05B 3/26* (2006.01)
*F28F 9/26* (2006.01)

(52) U.S. Cl.
USPC ........... 219/539; 219/213; 219/217; 219/537; 219/541; 219/549; 392/416; 392/433; 392/437; 392/438; 607/81; 607/100

(58) Field of Classification Search
None
See application file for complete search history.

(56) References Cited

U.S. PATENT DOCUMENTS

| | | | |
|---|---|---|---|
| 4,485,297 A * | 11/1984 | Grise et al. | 219/528 |
| 4,959,527 A | 9/1990 | Kivimaa et al. | |
| 4,998,006 A * | 3/1991 | Perlman | 219/212 |
| 5,399,996 A | 3/1995 | Yates et al. | |
| 5,410,127 A * | 4/1995 | LaRue et al. | 219/212 |
| 5,908,573 A * | 6/1999 | Chiles et al. | 219/545 |
| 5,912,811 A * | 6/1999 | Mackta | 363/45 |

(Continued)

FOREIGN PATENT DOCUMENTS

| | | |
|---|---|---|
| DE | 1615494 A1 | 2/1971 |
| DE | 3843074 A1 | 7/1989 |
| GB | 589752 A | 6/1947 |
| WO | WO0070270 | 11/2000 |

OTHER PUBLICATIONS

"EMF Documentation," Welcome to the Wellness Center, http://www.wellnesscenter.net/resources/articles/EMF/EMF_Doc.htm, printed Dec. 30, 2009, 3 pages.

(Continued)

*Primary Examiner* — Joseph M Pelham
(74) *Attorney, Agent, or Firm* — Fredrikson & Byron, P.A.

(57) ABSTRACT

Infrared heating panels are provided with an electrically insulative substrate that carries one or more infrared heating elements. Each heating element includes an elongated first segment attached to a first surface of the substrate and an elongated second segment electrically connected in series with the first segment. At least the first segment is a strip of an electrically resistive material adapted to emit infrared radiation in response to a current. The second segment is attached to the second surface of the substrate opposite from and in a parallel arrangement with the first segment such that a first current flowing through the heating element flows through the first segment in a first direction relative to the substrate and flows through the second segment in a second direction opposite the first direction. Saunas, heating systems, and methods for reducing electromagnetic emissions in an infrared sauna are also provided.

26 Claims, 22 Drawing Sheets

(56) References Cited

U.S. PATENT DOCUMENTS

| | | | |
|---|---|---|---|
| 6,734,404 B2* | 5/2004 | Hays | 219/552 |
| 6,745,411 B1* | 6/2004 | Kjonaas | 4/524 |
| 7,120,353 B2* | 10/2006 | Schaeffer et al. | 392/416 |
| 7,142,779 B2* | 11/2006 | Schaeffer et al. | 392/416 |
| 7,329,843 B2* | 2/2008 | Bikhovsky et al. | 219/528 |
| 2003/0156831 A1* | 8/2003 | Schaeffer et al. | 392/416 |
| 2004/0184793 A1* | 9/2004 | Schaeffer et al. | 392/416 |
| 2007/0145041 A1* | 6/2007 | Shim | 219/635 |
| 2011/0081135 A1 | 4/2011 | Felder | |

OTHER PUBLICATIONS

English Translation of Claims of DE 1615494 (German claims published Feb. 25, 1971; translated Nov. 18, 2011), 2 pages.
International Search Report for PCT/US2011/022215, dated Nov. 11, 2011, 13 pages.
Canadian Office Action for Application No. 2,729,500, dated Oct. 17, 2011, 3 pages.

* cited by examiner

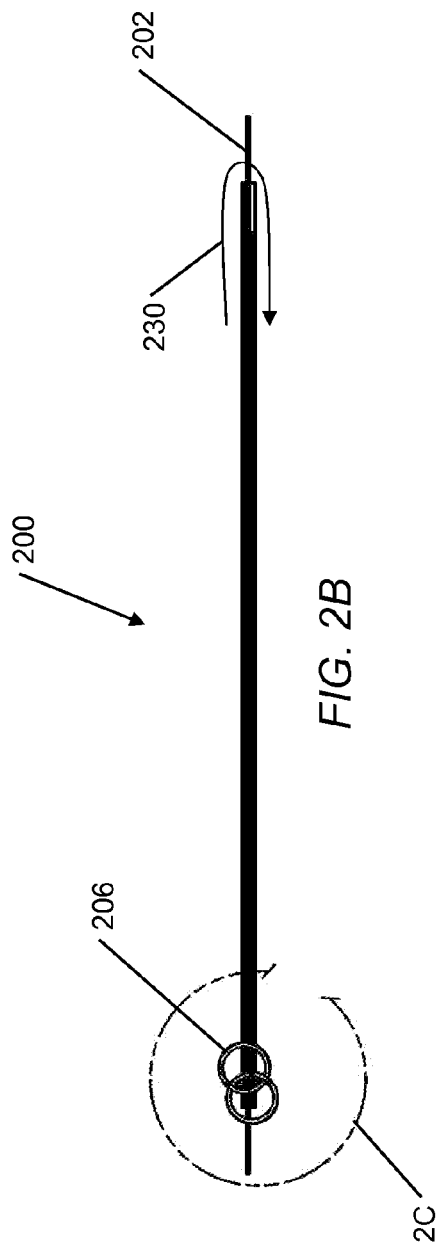
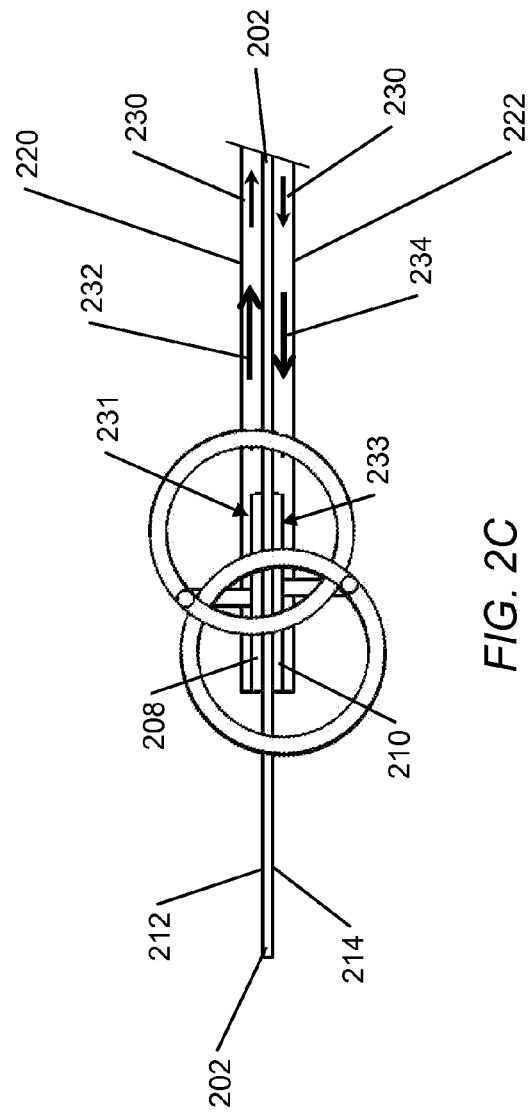

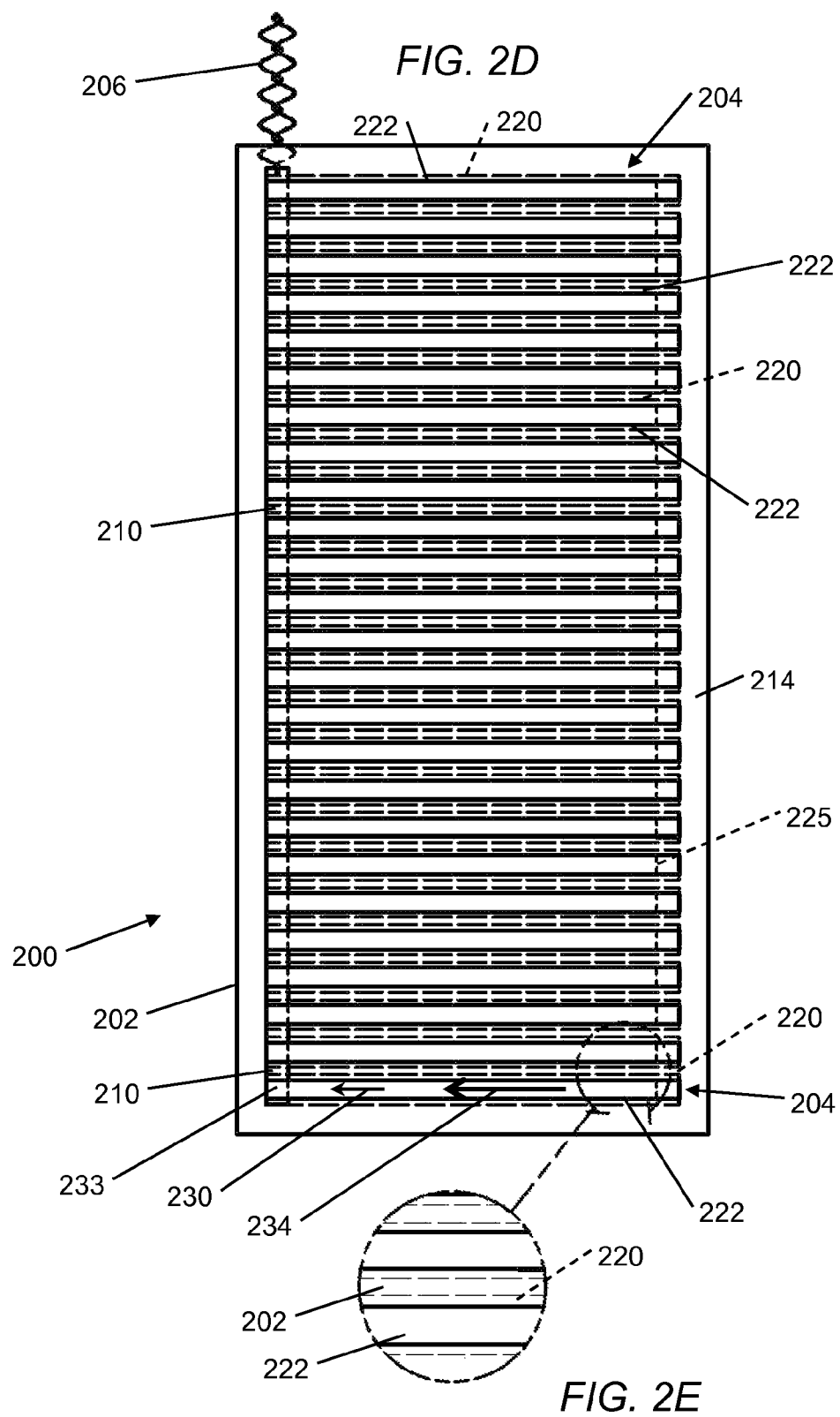

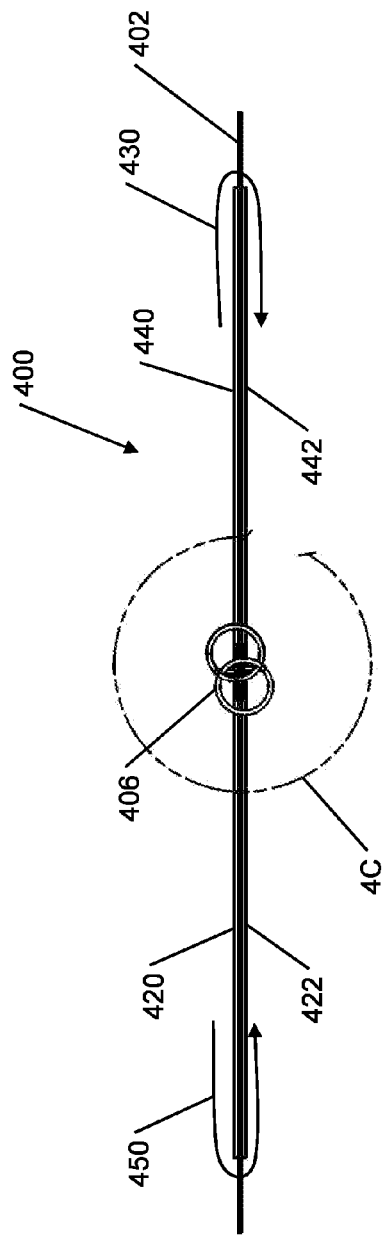
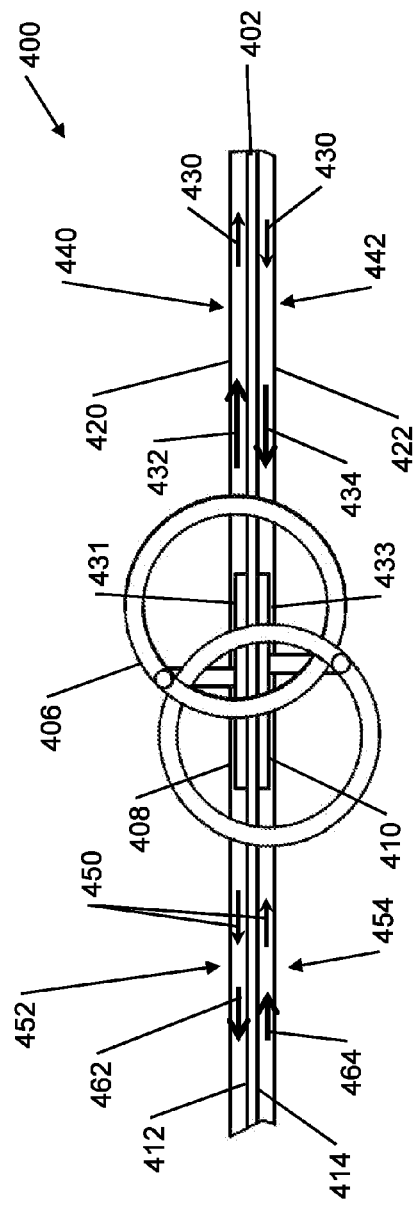

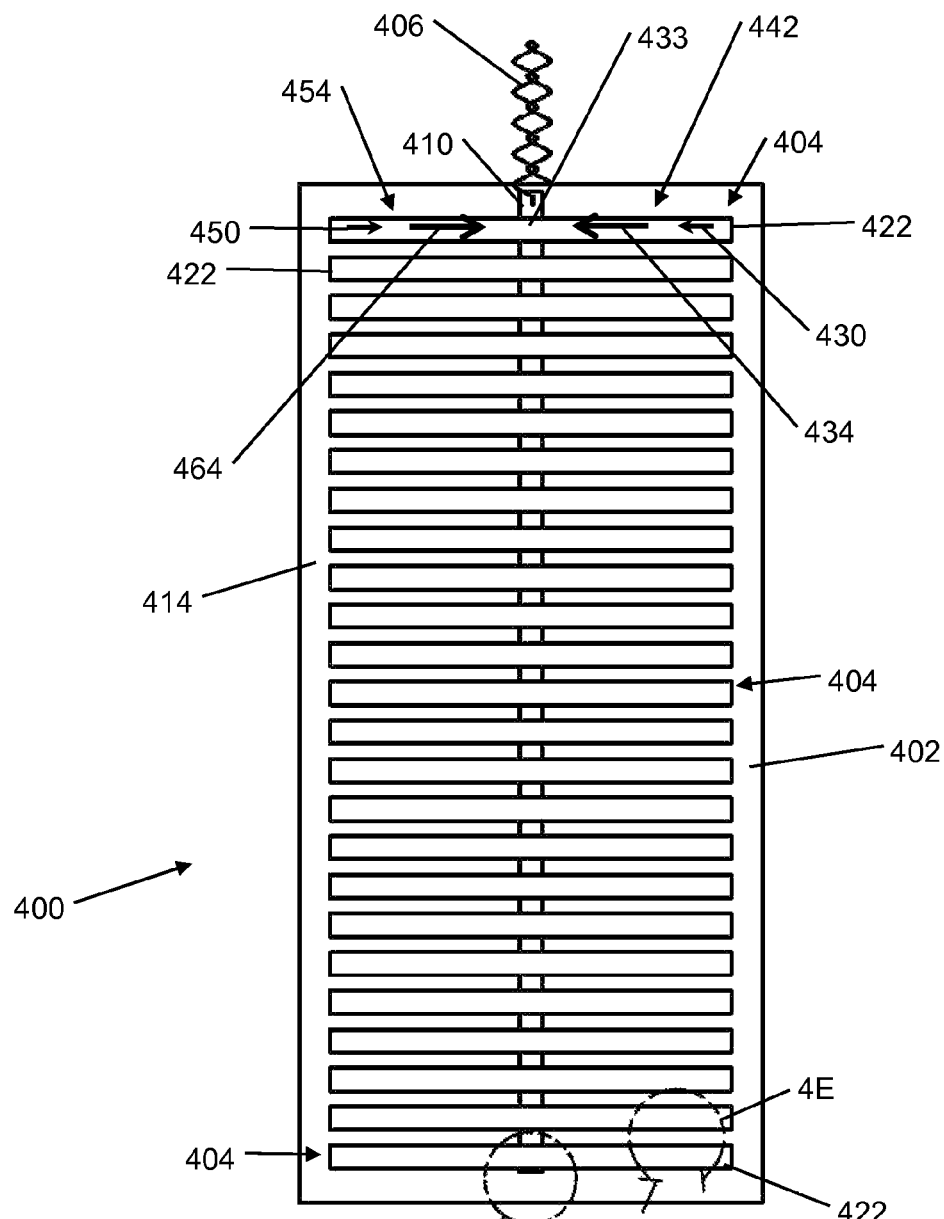

INFRARED HEATING PANELS, SYSTEMS AND METHODS

CROSS-REFERENCES

This application claims the benefit of U.S. Provisional Application No. 61/337,357 filed Feb. 2, 2010, the content of which is hereby incorporated by reference in its entirety.

FIELD

This disclosure relates generally to infrared saunas, and relates more particularly to infrared heating panels, systems and methods used for infrared saunas.

BACKGROUND

Sauna systems throughout history have employed various methods of heating a space to provide the therapeutic and cleansing effects of heat. As is well known, heat causes the human body to perspire and can also provide soothing and therapeutic effects to muscles and joints. Methods of heating a sauna include using open fires, enclosed stoves, and steam generators among others. While some forms of heat generation are effective to varying degrees, they can also present drawbacks. For example, the open fires found in old forms of Scandinavian saunas provided direct open flame heating, but also created intensely smoky rooms with short lived heat. Wood stoves enable a more controlled heat over a greater period of time, but also shield the heat due to the enclosed nature of the stove.

Saunas using electrically energized radiant heaters have also been developed. These systems employ infrared heating panels to generate electromagnetic radiation within the infrared spectrum. When absorbed by the body of a sauna user, the infrared radiation excites the molecules within the body to generate warming. Whereas steam or warm air generally only heat the skin and tissue directly beneath by conduction, infrared radiation more deeply penetrates the body (e.g., to about 1.5 inches) to more effectively and comfortably warm the body to a sweating temperature without the use of a conductive medium.

Radiant infrared heating systems are generally powered by conventional alternating current (AC) power sources, such as 110 volt, 60 Hz AC in the United States or 230 volt, 50 Hz AC in Europe. Such heating systems thus tend to generate some amount of low frequency (e.g., 50-60 Hz) electromagnetic (EM) radiation in addition to the desired infrared radiation utilized for heating. It has been estimated that in some cases infrared sauna systems may generate low frequency EM radiation with magnetic field levels as high as 60 milligauss. In comparison, areas under high voltage transmission lines have been measured with low frequency magnetic field levels as high as 1.9 milligauss and outdoor areas in open spaces have been measured with low frequency magnetic field levels as low as 0.3 milligauss.

Concerns about high levels of low frequency radiation have led to multiple methods for reducing the level of low frequency EM radiation in infrared heating systems. These include increasing the distance from the emitting source, reducing the exposure time to the radiation level and/or increasing shielding between the human body and the emitting source. Unfortunately, these methods are inherently limited for many sauna designs. For example, often exposure times cannot be controlled, or it may be impractical to reduce exposure time while also increasing distance between the human body and the emitting source. In addition, it may be difficult to increase distance given the normally confined nature of a sauna. Shielding the emitting source may undesirably reduce the effectiveness of the source, requiring longer exposure times and/or shorter distances to achieve similar effects. In addition, attempts have also been made to reduce the level of low frequency EM radiation through EM cancellation schemes, such as by producing multiple low frequency EM fields that tend to cancel one another.

SUMMARY

Some embodiments of the invention generally provide infrared heating panels, saunas, systems, and/or methods for generating heat. According to an aspect of the invention, an infrared heating panel is provided. The panel includes an electrically isolative planar substrate having a first surface and an opposing second surface and one or more infrared heating elements carried by the substrate. Each of the heating elements includes an elongated first segment attached to the first surface of the substrate and an elongated second segment attached to the second surface of the substrate. The second segment is positioned opposite from and in a parallel arrangement with the first segment. In addition, the first and the second segments are electrically connected in series such that a first current flowing through the heating element flows through the first segment in a first direction relative to the substrate and flows through the second segment in a second direction opposite the first direction. The first segment, and optionally the second segment, includes a strip of an electrically resistive material adapted to emit infrared radiation in response to the flow of the first current.

Another aspect of the invention provides an infrared heating panel including an electrically insulative planar substrate having a first surface and a second opposing surface and multiple infrared heating elements carried by the substrate. Each heating element has an elongated first segment attached to the first surface and an elongated second segment attached to the second surface opposite from and in a parallel arrangement with the first segment. The first segment includes a strip of an electrically resistive thin film adapted to emit infrared radiation in response to a current flow. The first segment and the second segment include a first electrical connection point and a second electrical connection point, respectively. The first and the second segments are electrically coupled so that a first current flowing between the first and the second connection points flows through the first segment in a first direction relative to the substrate. The first current also flows through the second segment in a second direction opposite the first direction.

Another aspect of the invention provides a method for reducing electromagnetic emissions in an infrared sauna. The method includes providing one or more infrared heating panels. Each heating panel has an electrically insulative planar substrate and at least one infrared heating element. The heating element includes an elongated first segment attached to a first surface of the substrate and an elongated second segment attached to a second surface of the substrate. The first and the second segments are electrically coupled together to provide a continuous conduction path. The method further includes producing a first current through the first segment to generate infrared radiation for heating a human in the infrared sauna. The first current flows through the first segment in a first direction relative to the substrate and generates a corresponding first electromagnetic field at frequencies below the infrared radiation. The method also includes flowing the first current through the second segment in a second direction relative to the substrate opposite the first direction. In doing so, the first current generates a corresponding second electromagnetic field that counteracts the first electromagnetic field.

Heating panels may include one, two, or any number of heating elements depending upon the design and desired functionality provided by a particular embodiment of the invention. In some cases, a heating panel may include multiple heating elements arranged on the substrate in a row between edges of the substrate. Heating element segments can be formed from a variety of materials that allow at least one of the segments to generate or emit infrared radiation in response to a current flow. In some cases at least one of the first and second segments is formed as a strip of electrically resistive material adapted to generate infrared radiation when energized with a current. In some cases both segments may be formed from the electrically resistive material. In some cases one of the segments is formed from an electrically conductive material.

In some embodiments power is provided to a heating panel via a first power bus and a second power bus. A variety of connection schemes can be used to power multiple heating elements. For example, a first power bus may coupled to each of the first segments of the heating elements proximate an end of the first segments while a second power bus may be coupled to each of the second segments of the heating elements proximate an end of the second segments. The first and the second segments may be coupled together opposite the power buses to provide a complete circuit with multiple heating elements connected in parallel across the two power buses. In another example, a first power bus is electrically coupled to the first segments of the heating elements between the ends of the segments (e.g., proximate a midpoint of the segments). Similarly, a second power bus may be electrically coupled to the second segments of the heating elements between the ends of the segments (e.g., proximate a midpoint of the second segments). The first and the second segments may be coupled together at both ends of the segments, providing multiple current paths between the power buses.

Infrared heating panels provided by some embodiments of the invention may optionally include one or more of a variety of elements in addition to one or more infrared heating elements. As just one example, in some cases an infrared heating panel assembly includes a back frame member and a front frame member enclosing a substrate and one or more infrared heating elements carried by the substrate. The panel assembly includes an electrical connection for connecting the one or more infrared heating elements to a source of alternating current, and also includes a thermal shielding layer. In some cases the front frame member includes one or more apertures and the thermal shielding layer is positioned between the one or more infrared heating elements and the one or more apertures.

Some embodiments of the invention can optionally provide one or more of the following features and/or advantages. Some embodiments provide an infrared heating panel that reduces selective EM field levels generated by the heating panel. For example, in some cases an infrared heating panel is configured with a specific geometric configuration and specific current polarities that generate multiple EM fields that counteract and/or cancel each other and thus tend to reduce the overall level of certain EM fields in the vicinity of the heating panel. In some cases the heating panels are designed to reduce the overall magnitude of AC generated low frequency radiation (e.g., 50 Hz or 60 Hz or other low frequency radiation below infrared frequency ranges) emanating from the heating panel, while also allowing generation of infrared EM radiation for heating a sauna user. In some embodiments an infrared heating panel/system may maintain certain low frequency magnetic field levels as low as, or below, 1.0 milligauss when measured at two inches above the heating element surface.

Some embodiments provide reduced EM field levels through the use of dual power buses connecting and powering multiple heating elements within a heating panel. In some cases the dual power buses are positioned on the substrate in a parallel configuration with opposite polarities to provide canceling EM fields generated by each of the buses. In some cases a single twisted wire pair feeds the parallel power buses at one location.

In some embodiments of the invention, infrared heating panels and systems are provided with a configuration that simplifies the system complexity while also delivering sufficient infrared heat and sufficiently low EM radiation levels at selected wavelengths. For example, in some cases a heating panel can be constructed with multiple carbon heating element traces printed on an electrically insulating substrate. Electrical leads may provide power to the heating traces and/ or in some cases conductive power strips may be printed, deposited, or otherwise included to electrically couple multiple heating elements. As just one example, manufacturing techniques for printed circuit boards can be used to print some heating element segments (e.g., electrically resistive carbon-based strips) on one side of a substrate and some heating element segments (e.g., inter-connecting conductive traces) on an opposite side of the substrate.

These and various other features and advantages will be apparent from a reading of the following detailed description.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 2B is an end view of the infrared heating panel of FIG. 2A along line 2B-2B.

FIG. 2C is an enlarged view of a portion of FIG. 2B.

FIG. 2D is a side surface view of the infrared heating panel of FIG. 2A.

FIG. 2E is an enlarged view of a portion of FIG. 2D.

FIG. 4B is an end view of the infrared heating panel of FIG. 4A along line 4B-4B.

FIG. 4C is an enlarged view of a portion of FIG. 4B.

FIG. 4D is a side surface view of the infrared heating panel of FIG. 4A.

FIG. 4E is an enlarged view of a portion of FIG. 4D.

DETAILED DESCRIPTION OF THE PREFERRED EMBODIMENTS

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
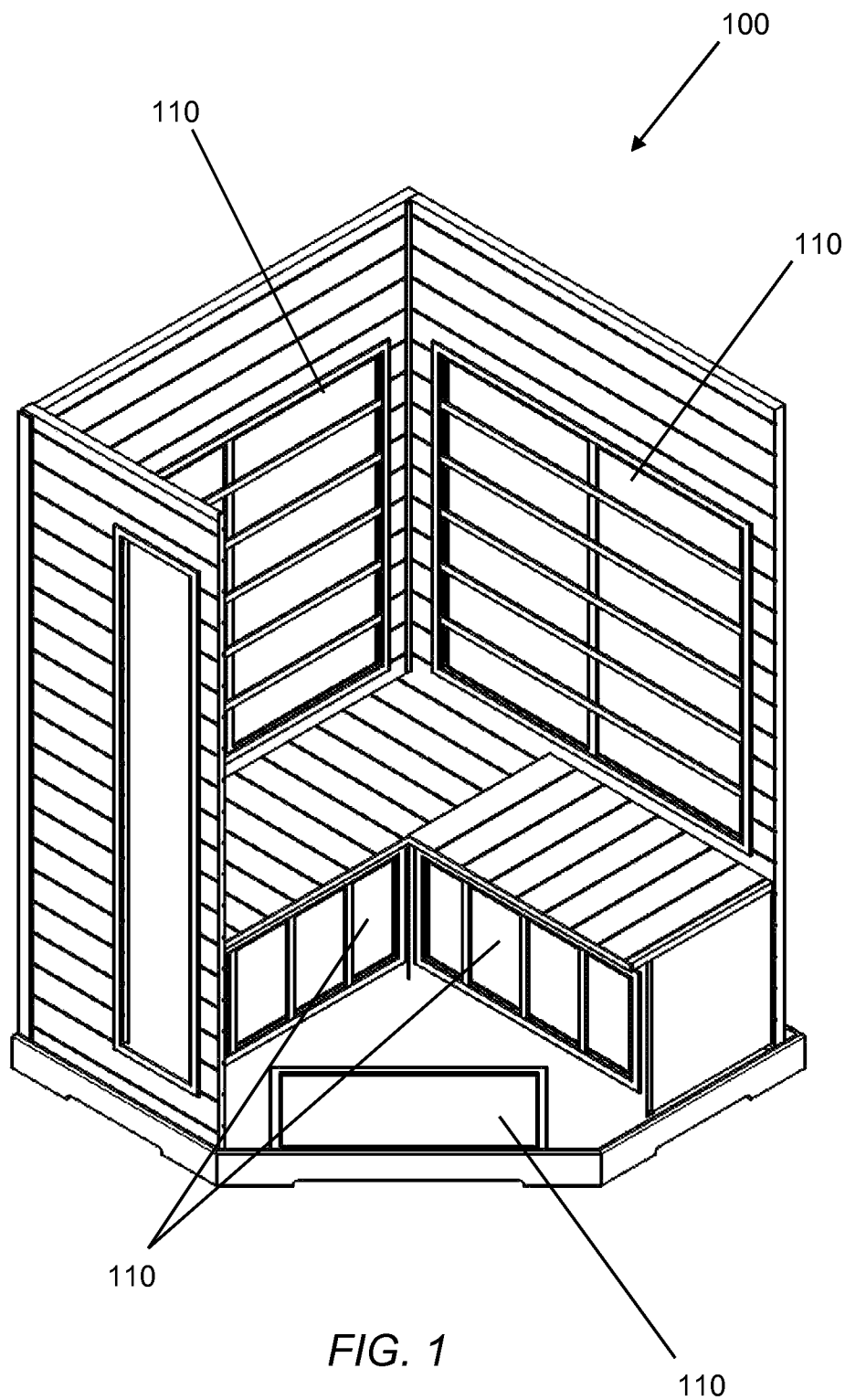
FIG. 1 is a perspective view of an infrared sauna according to some embodiments of the invention.

FIG. 1 is a perspective view of an infrared sauna 100 according to an embodiment of the invention. The sauna 100 includes a number of infrared heating panels 110 that, when powered, generate infrared radiation for warming a person within the sauna 100. It should be appreciated that the sauna 100 depicted in FIG. 1 is just one example of many possible designs and that it is contemplated that some embodiments of the invention may include a wide variety of sauna designs. In addition, the infrared heating panels 110 may be provided with a number of physical dimensions and configurations to accommodate the overall sauna design and provide a desired heating environment. Embodiments of the invention are not limited in this regard. For example, the sauna 100 shown in FIG. 1 includes a number of differently sized heating panels 110 positioned on the walls, floor, and bench of the sauna 100.

As will be discussed further herein, in some embodiments the heating panels 110 are configured to reduce the magnitude of certain EM fields generated by the heating panels 110. For example, in some cases the infrared heating panels 110 are configured to generate multiple EM fields that counteract and/or cancel each other and thus tend to reduce the overall level of certain EM fields in the vicinity of the heating panels. Reduced or cancelled EM fields can in some cases allow the heating panels 110 to be positioned in closer proximity to sauna users, thus increasing the effectiveness of the heating panels 110 while also reducing exposure to certain EM fields.

Figure 2A:
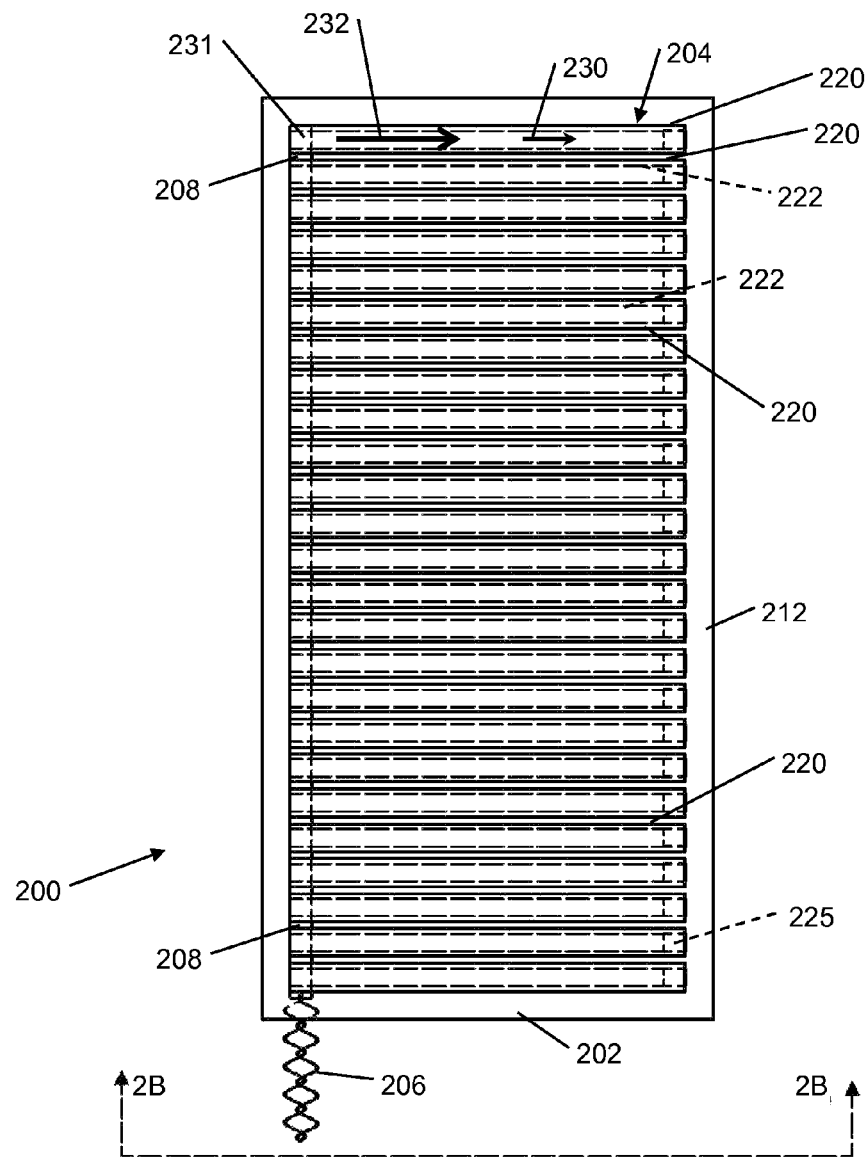
FIG. 2A is a side surface view of an infrared heating panel according to an embodiment of the invention.

FIGS. 2A and 2D are side views of opposite surfaces of an infrared heating panel 200 according to some embodiments of the invention. FIG. 2B is an end view of the infrared heating panel 200 from along line 2B-2B, and FIG. 2C is an enlarged end view of portion 2C shown in FIG. 2B. FIG. 2E is an enlarged view of portion 2E shown in FIG. 2D. In general, the heating panel 200 generates infrared radiation from electrical power, which can then be used to warm a person in close proximity to the panel. In some cases heating panels such as the heating panel 200 shown in FIG. 2A may be incorporated in a heating system including multiple heating panels, such as in an infrared sauna (e.g., as shown in FIG. 1). In some cases a heating panel may be useful by itself as a heat generating device. In addition, while several embodiments are described herein in the context of an infrared sauna, it should be appreciated that applications of a heating panel are not so limited and that heating panels in accordance with embodiments of the invention may be useful for many applications in a variety of environments in which a device is desired for producing radiant heat with infrared EM radiation.

The heating panel 200 generally includes a planar substrate 202 with multiple infrared heating elements 204 carried by the substrate 202. In this embodiment the heating panel 200 includes a twisted pair of power conductors 206 that can be connected to an electrical power supply to energize the panel 200. The twisted conductor geometry helps minimize additional EM field generation by the power conductors. The heating elements 204 are electrically coupled to the power conductors 206 in this case with a first power bus 208 and a second power bus 210 that serve to distribute the electrical power to the multiple heating elements 204. Of course, other methods of powering the heating elements 204 are also possible, including by individual twisted pair power conductors connecting each individual heating element 204 to the power source.

Referring to FIGS. 2B and 2C, the substrate 202 has a generally planar configuration with a first surface 212 (also shown in FIG. 2A) and a second surface 214 (also shown in FIG. 2D). The substrate 202 is constructed from an electrically insulative material (e.g., fiberglass) that provides a sturdy base for mounting or attaching the heating elements 204. For example, in some cases the substrate 202 is made from an FR-4 sheet of glass reinforced epoxy, such as in a printed circuit board. The size and dimensions of the substrate 202 can vary according to the space requirements needed for a particular design and the invention is not limited to any particular size and/or shape for the substrate. For example, FIG. 1 shows that the sauna 100 includes heating panels 110 of various sizes and configurations. In some cases, a heating panel and/or substrate may be between about 30 cm×15 cm and about 90 cm×60 cm.

Returning to FIGS. 2A-2E, the heating panel 200 includes multiple heating elements 204 arranged on the substrate 202 in a row, though it is contemplated that in some cases a heating panel may only include a single heating element or many more heating elements than are shown in the figures. Each heating element 204 includes a first segment 220 and a second segment 222 attached to the substrate 202. The first segment 220 of each heating element is formed from a strip of an electrically resistive (e.g., semi-conducting) material adapted to emit infrared radiation in response to a current flowing through the material. In the illustrated embodiment, the second segment 222 is formed from a strip of an electrically conductive material (e.g., a metal) attached to the second surface 214 of the substrate 202, thus providing a return path for a current flowing through the heating element 204. In certain cases the second segment 222 may optionally instead be formed from a strip of electrically resistive material, such as the same material used for the first segment 220.

As shown in this embodiment, the first and second segments 220, 222 of each heating element are electrically connected together in series at one end of the segments. The first segment 220 is attached to the first surface 212 of the substrate while the second segment 222 is attached to the second surface 214 of the substrate. The second segment 222 is attached to the substrate's second surface 214 opposite the substrate from and parallel to the first segment 220 on the substrate's first surface 212, in order to provide an EM field reducing/canceling configuration. The heating element segments are electrically coupled to the power conductors 206 via the first power bus 208 and the second power bus 210. For example, the first power bus 208 may provide the first segments 220 with a current at a positive voltage (e.g., 120 VAC), while the second power bus 210 connects the second segments 222 to AC ground. The power buses 208, 210 extend across opposite surfaces of the substrate 202 in a parallel configuration at one end of the heating elements, transverse to the lengthwise direction of the heating element segments. The multiple heating elements 204 are thus electrically coupled together in a parallel electrical configuration across the two power buses 208, 210.

The first segment 220 and the second segment 222 are elongated and stretch across the substrate 202 in a parallel arrangement with the second segment opposite the substrate from the first segment. The term parallel is used herein to describe a layout in which the first and the second segments for a given heating element extend along a common plane intersecting the segments perpendicular to the substrate. In some cases machine or method tolerances and/or practical manufacturing limitations may produce less than mathematically true or exact parallel alignment, but arrangements with these types of variations are still considered parallel for purposes of this disclosure. In addition, in some cases small variations from a true parallel arrangement may be acceptable depending upon the resulting functionality and desired performance criteria.

Referring to FIGS. 2A-2D, when a particular heating element 204 is energized, a current 230 flows through the heating element 204 between a first connection point 231 at the first power bus 208 to a second connection point 233 at the second power bus 210. As the current 230 flows through the first segment 220, it flows in a first direction 232 relative to the substrate 202 that is opposite a second direction 234 that it flows in the second segment 222. Because the same current 230 flows through both the first segment 220 and the second segment 222 of a particular heating element 204, the opposite polarity EM fields that are generated by the segments have the same or substantially the same magnitudes, leading to improved field canceling and low frequency EM field reduction.

The term "low frequency" is used generically herein to generally refer to EM radiation emanating from a heating panel at frequencies below the infrared radiation generated by the heating panel. Such frequencies may include, for example, very low frequencies (3-30 kHz), ultralow frequencies (300-3 kHz), super low frequencies (30-300 Hz), and/or extremely low frequencies (3-30 Hz), among other higher and lower ranges below infrared frequencies. As mentioned above, powering a conventional infrared heating panel with an alternating current can generate undesired low frequency or extremely low frequency EM radiation. For example, a 120 VAC, 60 Hz power input may lead to undesirably high levels of EM radiation at about 60 Hz. The heating panel 200 (along with other embodiments described herein) advantageously simplifies the system complexity compared to prior heating panels, while also delivering sufficient infrared heat and sufficiently reduced low frequency EM radiation levels, e.g., at 60 Hz.

Among other features, the parallel arrangement of the heating element segments 220, 222 on the substrate 202 reduces low frequency EM radiation by setting up the single current 230 flowing through both segments as determined by the overall load characteristics for the entire heating element. The current 230 tends to generate a first EM field as it passes through the first segment 220, with a polarity opposite to a second EM field that it generates as it passes through the second segment 222. The first and the second EM fields tend to counteract each other to reduce or substantially cancel the low frequency EM field levels emitted by a single heating element 204. The opposite polarity EM fields generated by the single current 230 have the same or substantially the same magnitudes, leading to improved field canceling and low frequency EM field reduction. As will be discussed further herein, an opposite and parallel arrangement of the first and the second power buses 208, 210 can provide similar benefits.

Heating panels according to some embodiments of the invention thus provide a simple and economical solution for reducing EM fields, especially when compared to prior systems in which separate conductors needed to be substantially identical in order to create substantially identical currents and fields with opposite polarity. For example, the inventors have found that with a configuration such as that shown in FIGS. 2A-2E, low frequency EM fields are reduced across substantially the entire panel 200 without spikes in non-cancelled peripheral EM fields. In testing an embodiment of the invention incorporating a design similar to that shown in FIGS. 2A-2E (e.g., powered at 120 VAC, 60 Hz), the inventors have found that certain measured low frequency magnetic field intensities are maintained at or below a 1.0 milligauss level at two inches from the panel across substantially the entire area of the heating elements 204. In further testing, the inventors found that certain low frequency magnetic field intensities are at or below a 1.5 milligauss level at two inches from the panel across substantially the entire length and width of the first and the second power buses 208, 210, in addition to the solder connection points between the power buses and the power conductors 206.

In some cases misalignment of the first and the second segments 220, 222 of a particular heating element 204 from a parallel arrangement on opposite sides of the substrate 202 can reduce cancellation of undesired EM fields. Thus it can be advantageous to precisely overlap the segments to the extent practical in order to maximize EM field cancellation. In some cases it may be acceptable to have some misalignment of the segments if less than maximum EM field cancellation is acceptable. As will be discussed further herein, the inventors have found that in some cases the configuration of the first and the second heating element segments 220, 222 has less of an effect upon the magnitude of certain low frequency EM radiation when compared with the effect caused by the first and the second power buses 208, 210. Accordingly, it may be more acceptable in some cases to allow greater amounts of misalignment between the heating element segments than the power buses, though numerous variations are of course possible.

In some cases cancellation of undesired EM fields can be improved by providing the first segment 220 and/or the second segment 222 of a particular heating element 204 with a particular width. For example, reducing the width of one or both segments may increase magnetic field cancellation outside the segments as the current distribution within the segments narrows (e.g., as the segments approach the behavior of wire conductors). One or both of the first and the second segments may be formed as a flat strip of material having a length and a width. In some cases the first segment 220, and optionally the second segment 222, is formed from a strip of resistive material with a width of about 2 cm. Of course this is just one example and other dimensions are also contemplated.

In some cases cancellation of undesired EM fields can be improved by providing the first segment 220 and/or the second segment 222 of a particular heating element 204 with matching dimensions. In certain embodiments, the width of the second segment 222 is substantially equal to the width of the first segment 220. In a preferred embodiment, the widths of the first and the second segments are substantially equal, and the segments are attached opposite each other on the substrate such that both segments are centered on and extend along a plane perpendicular to the substrate. This arrangement can provide a high degree of low frequency EM field cancellation, though it is not strictly required. For example, it is contemplated that the first segment and the second segment could potentially be offset a small amount, or could have different widths and/or be offset from an exact mirrored placement upon opposing surfaces of the substrate depending upon the level of EM field cancellation desired. As discussed below, reducing the width of one of the segments can save material costs while still providing adequate EM field cancellation.

Placing the first and the second segments closer together can also increase magnetic field cancellation. In some cases the substrate 202 may be extremely thin in order to reduce the gap between the segments while also maintaining electrical isolation along the lengths of the segments. As just a single example, in some cases the substrate may only be about 0.2 mm thick. Of course other dimensions are also contemplated.

In the embodiment shown in FIGS. 2A-2E, the first segments 220 of the heating elements 204 are each formed from a strip of an electrically resistive (e.g., semi-conducting) thin film attached to the first surface 212 of the substrate 202 and adapted to emit infrared radiation in response to a current flowing through the material. In some cases the material is a carbon-based thin film. The choice of resistive material and dimensions of the resistive material strip can vary depending upon the desired heat generation and performance characteristics (e.g., resistivity of the material). In one embodiment each of the first segments 220 are formed from a carbon-based resistive material having a resistivity of about 20 ohms per square centimeter at a thickness of 0.4 millimeters. A resistive thin film may be formed upon the substrate in any suitable manner, including by thin film deposition or etching. Another method of forming the thin film includes screen printing using a carbon based ink, such as a colloidal graphite ink. One example of a carbon-based material is described in U.S. patent application Ser. No. 12/573,882, the entire content of which is hereby incorporated by reference. U.S. Pat. No. 4,485,297 illustrates additional examples of resistive/semi-conductive materials, and its entire content is hereby incorporated by reference as well.

In certain embodiments the second segments 222 are each formed from a flat strip of an electrically conductive material attached to the second surface 214 of the substrate 202 opposite and parallel to a corresponding first segment 220. In some cases the conductive material is provided in the form of a flat, metal strip, such as a strip of copper or other suitable metal pressed into and/or adhered to the second surface 214 of the substrate. In certain embodiments the conductive material is a particulate material deposited upon the substrate. For example, a conductive material may be screen printed upon the substrate to provide the second segments. In this case the same or similar screen printing patterns can be used for the top and bottom surfaces of the substrate, therefore minimizing manufacturing complexity and variations. In addition, the second segments need not be a purely conductive material, but in some cases may instead be formed from a more resistive or semi-conductive material. In certain cases the second segments 222 may be formed from the same resistive material used to form the first segments 220, which can simplify material requirements.

Referring to FIG. 2A, the second segments 222 are shown in dashed lines, indicating they are placed on the second surface 214 on the other side of the substrate 202 from the first segments 220. FIG. 2D shows the first segments 220 in dashed lines, indicating they are placed on the first surface 212 or other side of the substrate 202 from the second segments 222. FIGS. 2A and 2D schematically illustrate the first segments 220 as being slightly wider than the second segments 222 to allow discernment of the different segments in the views. In some cases the first segment 220 may have a greater width than the second segment 222 (or vice versa). For example, the second segment 222 of electrically conductive material may be formed slightly narrower than the first segment of electrically resistive material. This option can save material costs by requiring less conductive material, while still providing adequate EM reduction characteristics. In some embodiments, though, the first and the second segments 220, 222 are formed with consistently identical, or substantially identical, widths and are placed on opposite surfaces of the substrate in an overlapping, parallel configuration. It should be appreciated that a number of configurations are contemplated for the widths of the segments. The choice of any particular configuration will depend upon the desired EM reduction characteristics.

Figure 2F:
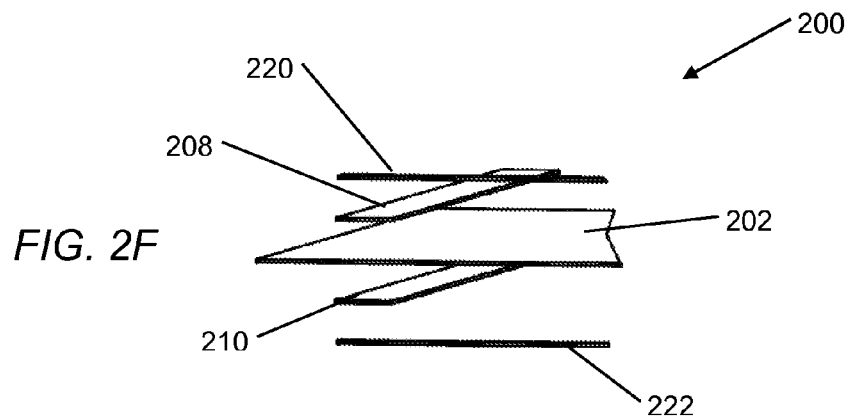
FIG. 2F is a partial, perspective exploded view of the infrared heating panel of FIG. 2A.
Figure 2G:
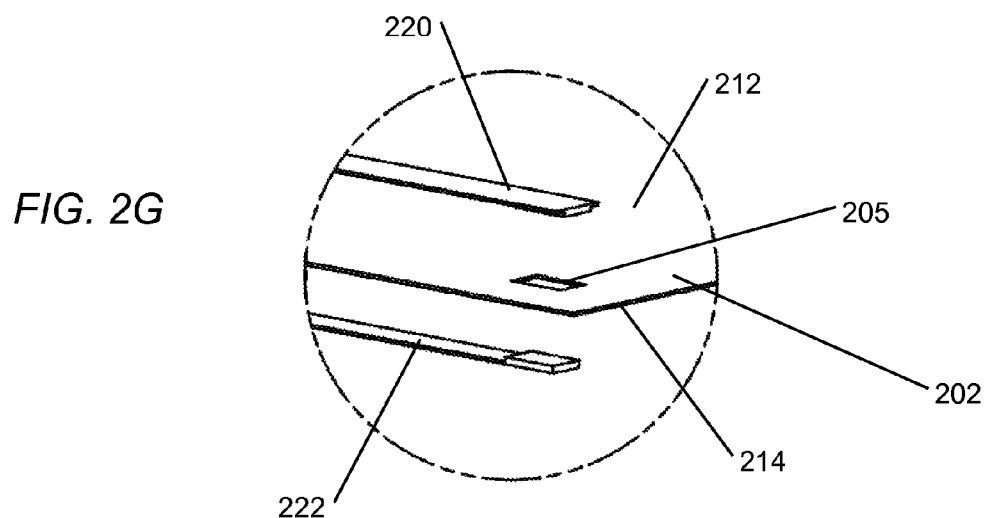
FIG. 2G is a partial, perspective exploded view of the infrared heating panel of FIG. 2A.

Turning to FIGS. 2A and 2D, the first and the second segments 220, 222 are electrically coupled together at one end of the segments, indicated schematically by a dashed square 225 at one end of the segments. In some cases a connection may be provided through the substrate 202 to electrically connect the overlaying segments 220, 222. Referring to FIG. 2G, in some cases the first and the second segments 220, 222 may be coupled together through the substrate 202 with a connection made through a void 205. FIG. 2G is a partial perspective, exploded view illustrating one possible manner for connecting segments of a single heating element in series. In this case multiple voids 205 (only one is illustrated) are formed in the panel substrate 202 in each location where a connection between a first segment 220 and a second segment 222 is planned. The voids 205 can be created in any suitable manner (e.g., drilled, cut, preformed, etc.). In some cases the voids 205 are substantially the same width as the heating element segments, though this is not a requirement in all cases.

According to one method of application, the second segments 222 of each heating element are applied/attached to the second surface 214 of the substrate, with each of the second segments 222 overlapping a void 205 in the substrate. The first heating element segments 220 are attached to the first surface of the substrate. In some cases a resistive material (e.g., a carbon-based thin film) is screen printed on the first surface 212 to form the first segments 220. The screen print also overlaps and fills the voids 205 extending through the thickness of the substrate 202 and making contact with each respective second segment 222 attached to the second surface 214. In some cases both the first and the second segments 220, 222 are screen printed, each filling a portion of the void 205.

In some embodiments narrower, slit-shaped voids may be provided in the panel substrate and a conductive strip or tab of material may be inserted through each void to electrically couple the heating element segments and the power buses. For example, a foil tab may be inserted through a void and then attached to the first surface of the substrate in the eventual location of a first heating element segment 220 and attached to the second surface of the substrate in the eventual location of a second heating element segment 222. The heating element segments can then be printed or otherwise applied over the surfaces of the substrate, overlapping with the portions of the tab to electrically couple the power bus and the heating element segment through the substrate.

Figure 2H:
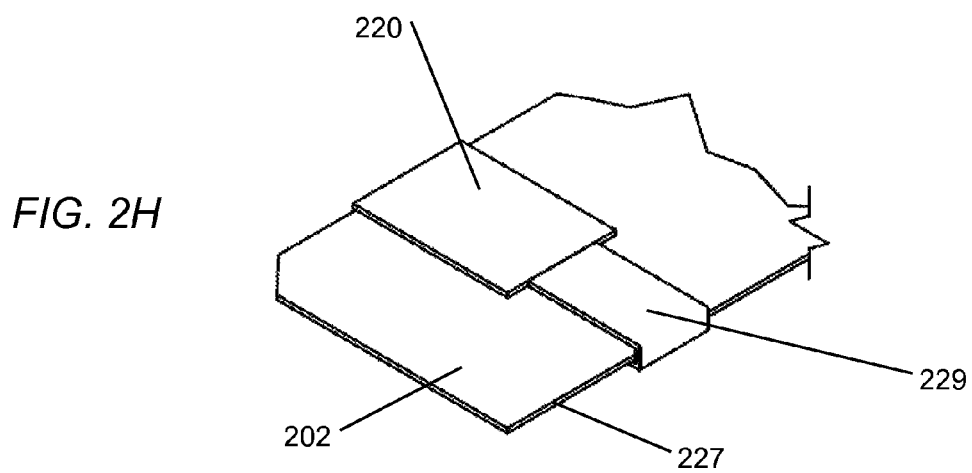
FIG. 2H is a partial perspective view of an infrared heating panel according to an embodiment of the invention.

Referring to FIG. 2H, in some cases the segments may instead be coupled together about an edge 227 of the substrate 202. For example, a strip 229 of conductive material (e.g., a metal foil strip or band) may be wrapped around the edge 227 of the panel substrate 202 and coupled to the first segment 220 and the second segment 222 (not shown). The electrical coupling between the strip 229 and the segments can be formed in any suitable manner, including soldering or adhering the strip to the substrate and then placing the first and the second segments over top of the strip. Further examples of such connections are discussed with respect to FIGS. 5-8.

Referring again to FIG. 2A, the first power bus 208 is attached to and extends across the first surface 212 of the substrate in a perpendicular orientation with the first segments of the heating elements. The first bus 208 electrically couples to the end of each first segment 220 (i.e., at junction 231) that is opposite the end of the first segment coupled to a respective second segment 222 (i.e., at junction 225). As shown in FIG. 2D, the second power bus 210 is attached to and extends across the second surface 214 of the substrate in a perpendicular orientation with the second segments of the heating elements. The second bus 210 electrically couples to the end of each second segment 222 (i.e., at junction 233) that is opposite the end of the second segment coupled to a respective first segment 220 (i.e., at junction 225). The second power bus 210 is attached to the substrate opposite from the first power bus 208 in a parallel arrangement. As will be discussed further herein, this parallel and opposite arrangement can reduce the magnitude of unwanted low frequency EM fields emanating from the power buses.

The first and the second power buses 208, 210 may be formed from any suitable electrically conductive material, such as a metal (e.g., copper or another other metal or alloy). In the illustrated embodiment, the first and the second power buses 208, 210 are each formed from a flat metal strip that is secured to the substrate 202 during a laminating process similar to construction of a printed circuit board. Of course, metal strips may be attached in other ways, including for example, with an adhesive, welding, or another mechanism. In certain embodiments the first and/or the second power buses may alternatively be formed with a different process such as screen printing, etching, deposition, or another type of formation methods.

In certain embodiments the heating panel 200 may be conveniently produced by providing the electrically insulative substrate 202 and then attaching the first power bus 208 to the substrate (e.g., through mechanical attachment of a metal strip or screen printing a conductive particulate material). Multiple carbon traces can then be printed on the first surface 212 of the substrate to provide multiple first segments 220 overlapping and electrically connected to the first power bus. The substrate 202 is then turned over and the second power bus 210 and multiple second segments 222 are attached to the second surface 214 in a similar manner.

The first and the second power buses 208, 210 can be coupled to the first segments 220 and the second segments 222 of the heating elements 204 in any suitable manner. Turning to FIGS. 2C and 2F, in some cases the power buses and the heating element segments are sandwiched together about the substrate 202 in a laminating process. For example, as shown in FIG. 2C, in this embodiment the first power bus 208 is placed (e.g., deposited, formed, attached, etc.) on the first surface 212 of the substrate 202, and the second power bus 210 is placed on the second surface 214 of the substrate 202. The first segments 220 of electrically resistive material are then formed over top of the first surface 212 of the substrate as well as over top of the first power bus 208, providing a secure and reliable coupling between the first power bus and the first segments. A similar procedure can be used to attach the second segment 222 to the substrate's second surface 214 and the second power bus 210. Thus, the panel 200 is formed as a laminate having multiple layers proximate to the electrical connections between the heating element and the power buses. Specifically, in the illustrated embodiment, the laminate includes in order from top down shown in FIG. 2C, the first segment 220, the first power bus 208, the substrate 202, the second power bus 210, and the second segment 222. Of course other layers may also be present in between or outside of the illustrated stack. For example, in some cases an outer insulative layer may be placed adjacent the first segment 220 and also adjacent the second segment 222 to electrically insulate the entire panel 200.

Figure 3:
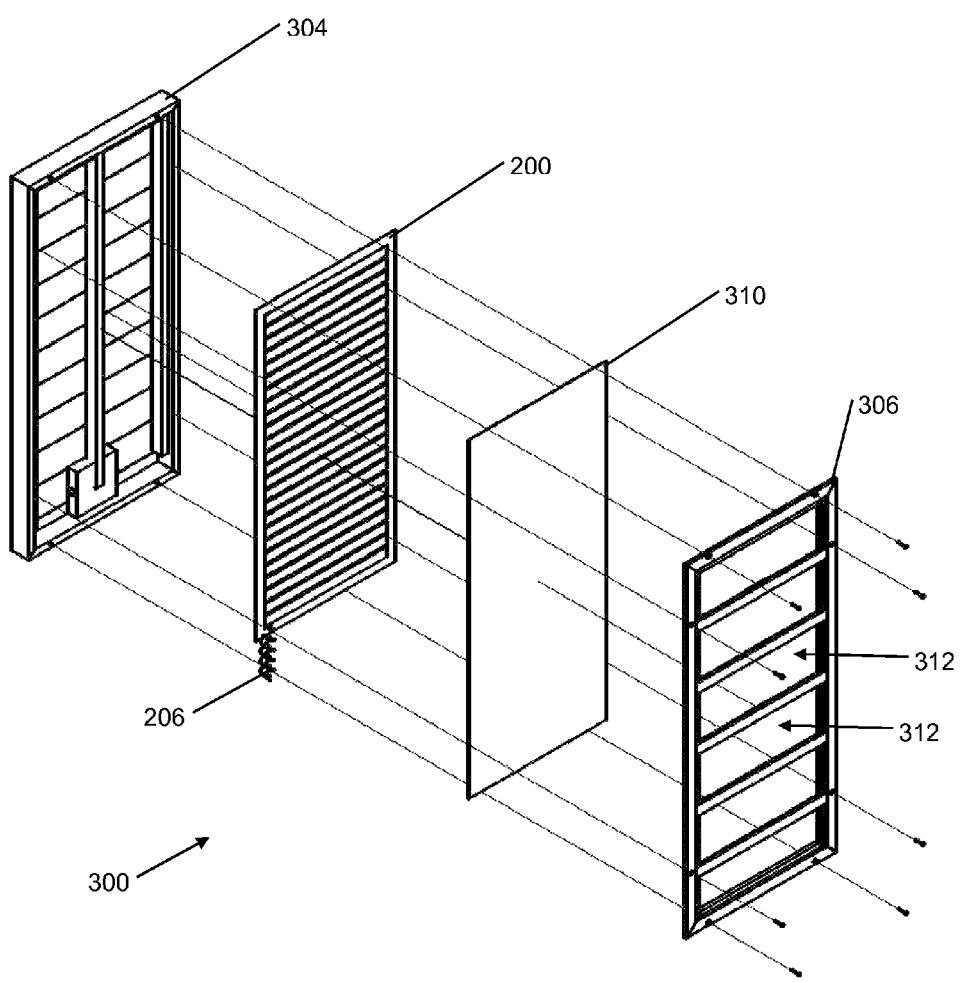
FIG. 3 is an exploded assembly view of an infrared heating panel assembly according to an embodiment of the invention.

FIG. 3 is an exploded assembly view of an infrared heating panel assembly 300 according to some embodiments of the invention. The panel assembly 300 generally provides an enclosure for a heating panel, such as the heating panel 200 described above with respect to FIGS. 2A-2E. In certain embodiments the panel assembly includes a back frame member 304 and a front frame member 306 that enclose the heating panel 200 and are coupled with fastening members such as screws. The panel assembly 300 includes an electrical connection, such as the power conductors 206 described above, for connecting the infrared heating panel 200 to a source of alternating current. The panel assembly 300 also includes a thermal shielding layer 310 that can be useful for shielding a sauna user from incidental or temporary contact with the heating elements. For example, the thermal shielding layer 310 may be a cloth panel that provides a mild thermal conductivity barrier to act as a thermal shield to minimize discomfort to human skin in the event of direct contact. In some cases the front frame member 306 includes one or more apertures or windows 312 to facilitate radiation/heat flow and the thermal shielding layer 310 is positioned between the panel 200 and the apertures 312.

According to some embodiments, the thermal shielding layer 310 also acts as a ground plane to shield a sauna user from electric fields generated by the heating panel. In some cases the thermal shielding layer 310 is formed from a conductive fabric and then connected by wire to ground potential through, e.g., the power conductors, the panel frame, a conduit, or another suitable surface or component at ground potential.

Figure 4A:
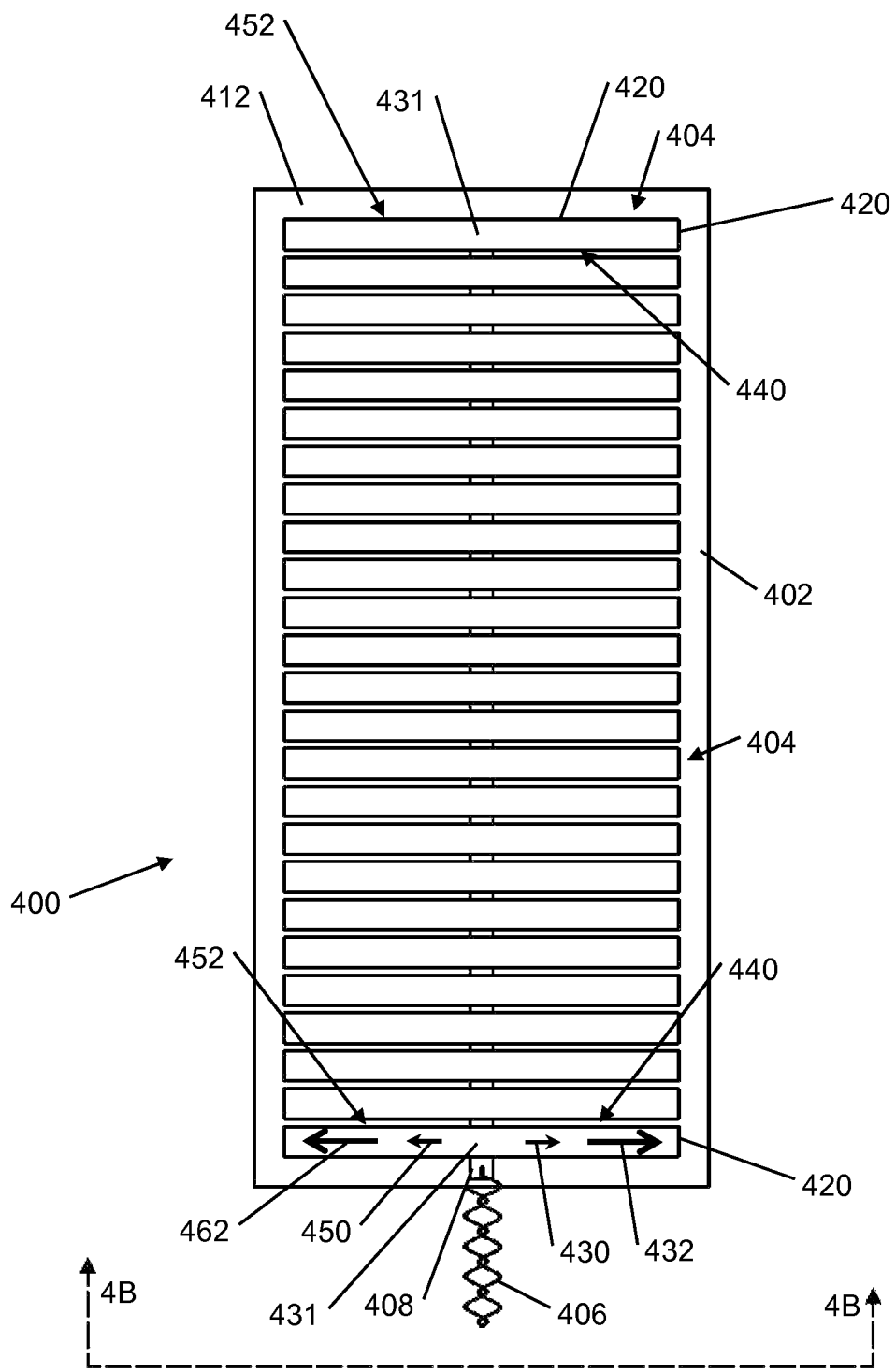
FIG. 4A is a side surface view of an infrared heating panel according to an embodiment of the invention.
Figure 4F:
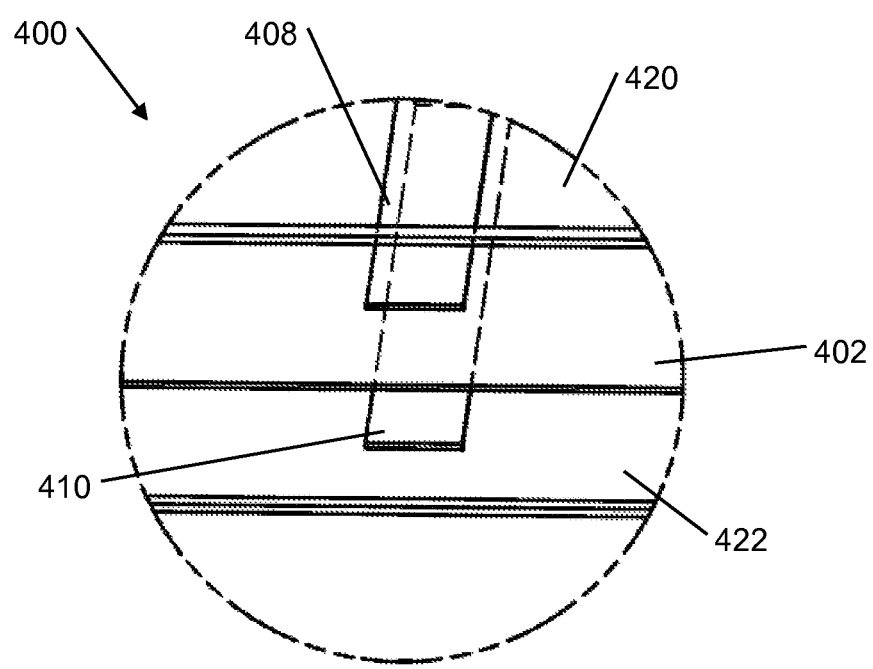
FIG. 4F is a partial, perspective exploded view of the infrared heating panel of FIG. 4A.

FIGS. 4A and 4D are side views of opposite surfaces of an infrared heating panel 400 according to some embodiments of the invention. FIG. 4B is an end view of the infrared heating panel 400 from along line 4B-4B, and FIG. 4C is an enlarged end view of portion 4C shown in FIG. 4B. FIG. 4E is an enlarged view of portion 4E shown in FIG. 4D. FIG. 4F is an enlarged view of portion 4F shown in FIG. 4D. The heating panel 400 generally includes a planar substrate 402 with multiple infrared heating elements 404 carried by the substrate 402. In this embodiment the heating panel 400 includes a twisted pair of power conductors 406 that can be connected to an electrical power supply to energize the panel 400. The heating elements 404 are electrically coupled to the power conductors 406 in this case with a first power bus 408 and a second power bus 410, which serve to distribute the electrical power to the multiple heating elements 404.

In the illustrated embodiment the substrate 402 has a generally planar configuration with a first surface 412 and a second surface 414, and is constructed from an electrically insulative material (e.g., an FR-4 circuit board) for mounting or attaching the heating elements 404. Each heating element 404 includes a first segment 420 and a second segment 422 that are electrically coupled together. The first and the second segments 420, 422 are elongated and stretch across the substrate 402 in a parallel and spaced apart configuration, and are electrically coupled together at both ends of the segments. The multiple heating elements 404 are arranged on the substrate 402 in a row, with the individual segments of the heating elements in a parallel configuration.

As is shown, the first segment 420 of each heating element 404 is attached to the first surface 412 of the substrate 402 and the second segment 422 of each heating element 404 is attached to the second surface 414 of the substrate 402. The second segment 422 is attached to the substrate's second surface 414 opposite the substrate from and in a parallel arrangement with the first segment 420 on the substrate's first surface 412, in order to provide a low frequency EM field reducing/canceling configuration.

The heating element segments are electrically coupled to the power conductors 406 via the first power bus 408 and the second power bus 410. In this embodiment the power buses 408, 410 extend across opposite surfaces of the substrate 402 perpendicular to the lengthwise direction of the first and the second segments. The second power bus 410 is attached to the second surface 414 of the substrate opposite from and in a parallel arrangement with the first power bus 408, which is attached to the first surface 412 of the substrate.

In certain cases the power buses 408, 410 connect to the first and the second segments 420, 422 of the heating elements at a point between the ends of the heating element, rather than at one end as in FIGS. 2A-2E. As is shown, the first power bus 408 is connected to the first segments 422 at approximately the midpoint of the first segments, while the second power bus 410 is connected to the second segments 422 at approximately the midpoint of the second segments. Thus, by coupling to the first and the second segments 420, 422 at approximately their midpoints, the first and the second power buses 408, 410 create multiple parallel connections and current paths through separate portions of the first and the second segments between the power buses.

In the embodiment shown in FIGS. 4A-4E, the first segments 420 of the heating elements 404 are each formed from a strip of an electrically resistive thin film attached to the first surface 412 of the substrate 402 and adapted to emit infrared radiation in response to a current flow. For example, in some cases the first segments 420 are formed from a carbon-based thin film, such as is described with respect to FIGS. 2A-2E. In this embodiment the second segments 422 are each formed from a strip of an electrically conductive material (e.g., a metal) attached to the second surface 414 of the substrate 402 opposite and parallel to a corresponding first segment 420. Other materials, including printed and/or resistive materials are also contemplated for the second segments 422.

Referring to FIG. 4E, the second segments 422 are shown in dashed lines, indicating they are placed on the second surface 414 or other side of the substrate 402 from the first segments 420. FIG. 4E schematically illustrates the first segments 420 as being slightly wider than the second segments 422 to allow discernment of the different segments in the views. In some embodiments, though, the first and the second segments 420, 422 are formed with consistently identical, or substantially identical, widths and are placed on opposite surfaces of the substrate in an overlapping, parallel configuration.

The first and the second segments 420, 422 are electrically coupled together at both ends of the segments. In some cases the segments may be coupled together through the substrate 402 with a connection made through a void (not shown), as discussed with respect to FIG. 2G. In some cases the segments may instead be coupled together about the edges of the substrate (not shown), such as with a conductive foil strip or band, in a similar manner to the configuration described with respect to FIG. 2H.

In the example shown in FIGS. 4A-4F, the power buses 408, 410 extend transverse to the segments between the end connections of the first and the second segments. Referring again to FIG. 4A, the first power bus 408 extends across (e.g., underneath) and electrically couples to the first segments 420 at approximately the midpoint of the segments 420 (other points of connection are also contemplated). As shown in FIG. 4D, the second power bus 410 extends across and electrically couples to the second segments 422 at approximately the midpoint of the segments 422. The first and the second power buses 408, 410 can be coupled to the first segments 420 and the second segments 422 of the heating elements 404 in any suitable manner. Turning to FIGS. 4C and 4F, in some cases the power buses and the heating element segments are sandwiched together about the substrate 402 in a laminating process. For example, as shown in FIG. 4C, the first power bus 408 is placed (e.g., deposited, formed, attached, etc.) on the first surface 412 of the substrate 402, and the second power bus 410 is placed on the second surface 414 of the substrate 402. The first segment 420 of electrically resistive material is then formed over top of the first surface 412 of the substrate as well as over top of the first power bus 408, providing a secure and reliable coupling between the first power bus and the first segment. A similar procedure can be used to attach the second segment 422 to the substrate's second surface 414 and the second power bus 410.

Thus, the panel 400 is formed as a laminate having multiple layers proximate to the electrical connections between the heating element and the power buses. Specifically, in the illustrated embodiment the laminate includes in order from top down shown in FIG. 4C, the first segment 420, the first power bus 408, the substrate 402, the second power bus 410, and the second segment 422. Of course other layers may also be present in between or outside of the illustrated stack. For example, in some cases an outer insulative layer may be placed adjacent the first segment 420 and also adjacent the second segment 422 to electrically insulate the entire panel 200.

Referring to FIGS. 4A-4D, when a particular heating element 404 is energized, a first current 430 flows through a first portion 440 of the first segment and a first portion 442 of the second segment between a first connection point 431 at the first power bus 408 to a second connection point 433 at the second power bus 410. As the first current 430 flows through the first portion 440 of the first segment 420, it flows in a first direction 432 relative to the substrate 402 that is opposite a second direction 434 that it flows in the first portion 442 of the second segment 422. In addition, a second current 450 flows through a second portion 452 of the first segment and a second portion 454 of the second segment between the first connection point 431 and the second connection point 433. As the second current 450 flows through the second portion 452 of the first segment 420, it flows in a first direction 462 relative to the substrate 402 that is opposite a second direction 464 that it flows in the second portion 454 of the second segment 422. Because the same first current 430 flows through both first portions of the first and second segments, and the same second current 450 flows through both second portions of the first and the second segments, the opposite polarity EM fields that are generated by the portions of the segments have the same or substantially the same magnitudes, leading to improved field canceling and low frequency EM field reduction.

Figure 5A:
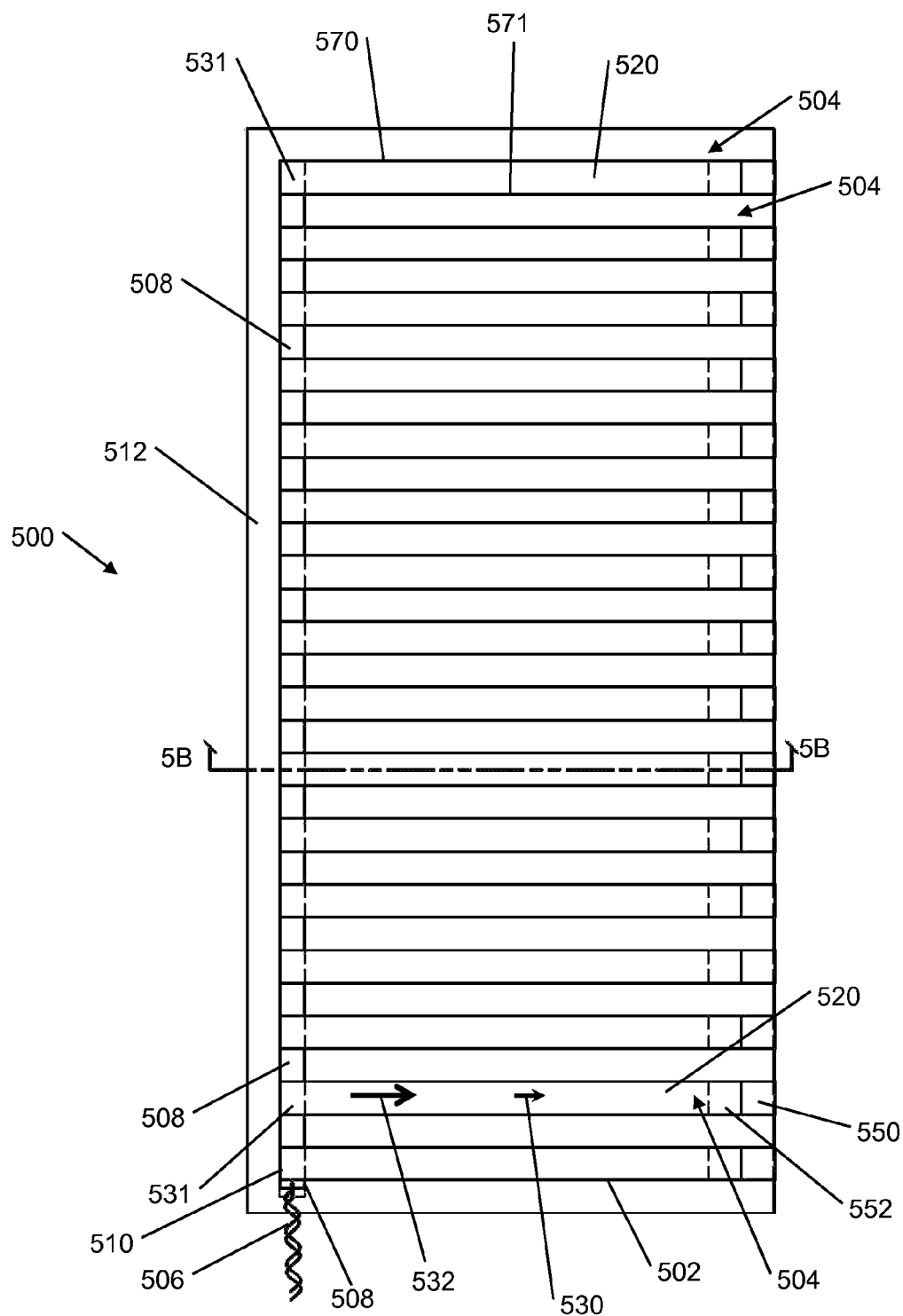
FIG. 5A is a side surface view of an infrared heating panel according to an embodiment of the invention.
Figure 5B:
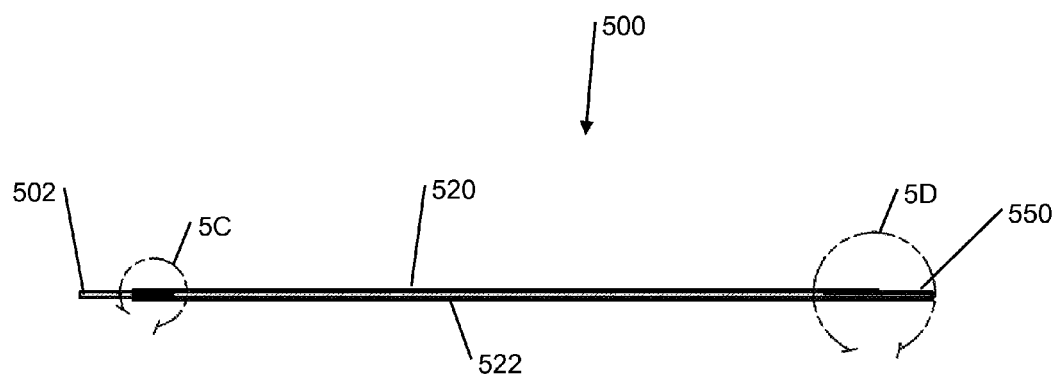
FIG. 5B is a cross-sectional view of the infrared heating panel of FIG. 5A along line 5B-5B.
Figure 5C:
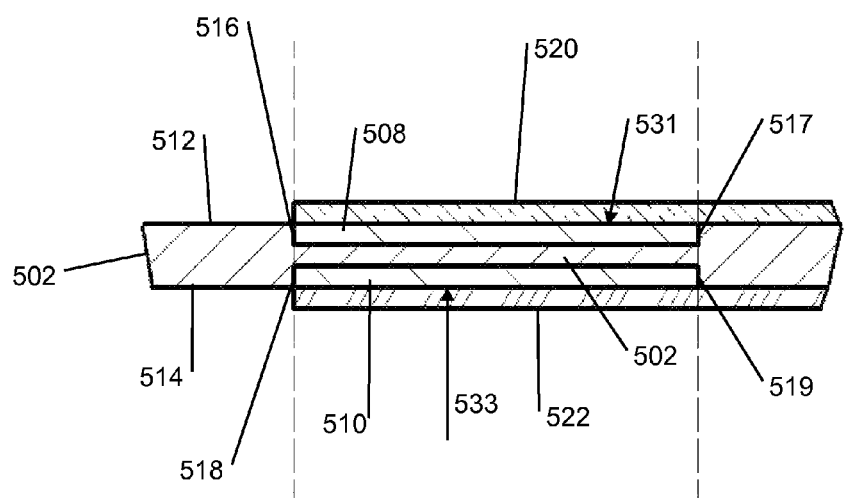
FIG. 5C is an enlarged view of one end of the infrared heating panel shown in FIG. 5B.
Figure 5D:
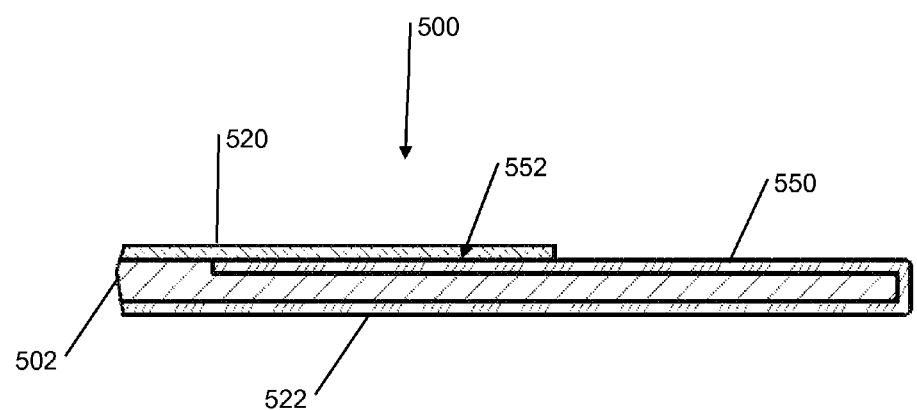
FIG. 5D is an enlarged view of another end of the infrared heating panel shown in FIG. 5B.

FIG. 5A is a side surface view of an infrared heating panel 500 according to an embodiment of the invention. FIG. 5B is an end view of the infrared heating panel 500 from along line 5B-5B, and FIG. 5C is an enlarged end view of portion 5C shown in FIG. 5B. FIG. 5D is an enlarged view of portion 5D shown in FIG. 5B. In general, the heating panel 500 generates infrared radiation from electrical power, and is useful for generating heat such as in the infrared sauna 100 shown in FIG. 1. The heating panel 500 is similar in many respects to the heating panel 200 discussed with respect to FIGS. 2A-2E, and portions of that discussion are also applicable to the embodiment shown in FIGS. 5A-5F.

The heating panel 500 includes a substrate 502 that carries multiple heating elements 504 positioned in a row across the panel. Each heating element 504 includes a first segment 520 attached to a first surface 512 of the substrate and a second segment 522 attached to a second surface 514 of the substrate 502. The first and second segments 520, 522 are electrically connected together in series at one end of the segments, in this embodiment about an edge of the substrate 502. The segments are electrically coupled to power conductors 506 via a first power bus 508 and a second power bus 510. Similar to the embodiment in FIGS. 2A-2E, the power buses 508, 510 extend across opposite surfaces of the substrate 502 in a parallel configuration at one end of the heating elements.

The second segment 522 is attached to the substrate's second surface 514 opposite the substrate from and parallel to the first segment 520 on the substrate's first surface 512, in order to provide an EM field reducing/canceling configuration. In a preferred embodiment, the widths of the first and the second segments are substantially equal, and the segments are attached opposite each other on the substrate such that both segments are centered on and extend along a plane perpendicular to the substrate. FIG. 5F shows the first segment 520 and the second segment 522 of a single heating element 504 in cross-section. As shown, the first and the second segments are attached opposite each other on the substrate 502 such that corresponding first edges 570, 572 of the segments are substantially aligned and corresponding second edges 571, 573 are substantially aligned. This arrangement can provide a high degree of low EM field cancellation, though it is not strictly required.

As in the embodiment shown in FIGS. 2A-2E, when a particular heating element 504 is energized, a current 530 flows through the heating element 504 between a first connection point 531 at the first power bus 508 to a second connection point 533 at the second power bus 510. As the current 530 flows through the first segment 520, it flows in a first direction 532 relative to the substrate 502 that is opposite a second direction that it flows in the second segment 522. Because the same current 530 flows through both the first segment 520 and the second segment 522 of a particular heating element 504, the opposite polarity EM fields that are generated by the segments have the same or substantially the same magnitudes, leading to improved field canceling and low frequency EM field reduction.

As in the embodiment in FIGS. 2A-2E, the first power bus 508 extends across and is attached to the first surface 512 of the substrate to electrically connect each of the first segments 520 of the heating elements 504 to the panel's power conductors 506. The second power bus 510 (electrically coupled to each of the second segments 522 of the heating elements) is attached to the second surface 514 of the substrate 502, opposite from and in a parallel arrangement with the first power bus 508. The first and the second power buses 508, 510 may be formed from any suitable electrically conductive material, such as a metal (e.g., copper or another other metal or alloy). In the illustrated embodiment, the first and the second power buses 508, 510 are each formed from a flat metal strip that is secured to the substrate 502 during a laminating process similar to construction of a printed circuit board. As shown, in some cases the power buses are placed adjacent to the surfaces of the substrate and pressed into the substrate, flush with the substrate surfaces 512, 514 as part of the laminating process. Of course, metal strips may be attached in other ways, including for example, with an adhesive, welding, or another mechanism. In certain embodiments the first and/or the second power buses may alternatively be formed with a different process such as screen printing, etching, deposition, or another type of formation methods.

The placement of the first power bus 508 and the second power bus 510 between the power conductors 506 and the heating elements 504 set up currents of opposite polarity within the first and the second power buses. According to some embodiments of the invention, the first and the second power buses 508, 510 are preferably configured to reduce the magnitude of unwanted low frequency EM fields emanating from the heating panel 500. The inventors have found that in some cases the configuration of the first and the second power buses has an increased effect upon the magnitude of certain low frequency EM radiation when compared with the effect caused by individual heating elements 504. It is believed that relatively high levels of current flowing through the power buses in comparison to the current levels in each heating element 504 contribute to this effect.

In certain embodiments, the second power bus 510 is attached to the second surface 514 of the substrate opposite from and in a parallel arrangement with the first power bus 508. For example, in some cases the first power bus 508 and the second power bus 510 extend along a common plane intersecting the power buses perpendicular to the substrate 502. As shown in FIG. 5C, in some cases the first and the second power buses can be considered to be centered along a common plane (not shown). In addition, in some cases the width of the second bus 510 is substantially equal to the width of the first bus 508. In a preferred embodiment the widths of the first and the second power buses are substantially equal, and the buses are attached opposite each other on the substrate 502 such that corresponding first edges 516, 518 of the buses are substantially aligned and corresponding second edges 517, 519 are substantially aligned (as shown by the dashed lines in FIG. 5C). FIGS. 6A-6D are simplified views of the heating panel 500 without the heating elements 504, providing a cleaner view of the opposite and parallel arrangement of the power buses. This arrangement of the power buses can provide a high degree of low frequency EM field cancellation, though it is not strictly required in all cases. For example, it is contemplated that the first power bus and the second power bus could potentially be offset a small amount, or could have different widths and/or be offset from an exact mirrored placement upon opposing surfaces of the substrate depending upon the level of EM field cancellation desired.

According to some embodiments, the configuration of the connections between the heating elements and the first power bus and/or the second power bus can also reduce the magnitude of unwanted low frequency EM fields emanating from a heating panel. In some cases each connection between the first segments of the heating elements and the first power bus is substantially identical to and matched by each corresponding connection between the second segments and the second power bus. It is believed that substantially identical or mirrored connections can contribute to increased cancellation of unwanted low frequency EM fields, though substantial identity is not strictly required in all embodiments. For example, one or more imperfectly matched connections providing less than ideal cancellation may be sufficient in some cases based on tradeoffs in performance, cost, manufacturing tolerances, and other such factors.

Referring to FIGS. 5A and 5C, the first segments 520 of the heating elements extend across the substrate 502 perpendicular to the first power bus 508 and connect to the power bus 508 at one end (at the left end as illustrated in FIG. 5A). In this embodiment, each of the first segments 520 overlaps the entire width of the first power bus 508, extending across the width to end substantially flush with the first edge 516 of the bus. Extending the first segments 520 across the entire width of the bus can provide a more uniform junction 531 across the width of the bus. It is believed that this leads to more uniform and consistent current densities in the first power bus 508, which can be more easily matched by the configuration of the second power bus and heating element second segments on the second surface 514 of the substrate. Referring to FIG. 5C, in some cases each of the second segments 522 overlaps the entire width of the second power bus 510, extending across the width to end substantially flush with the first edge 518 of the second power bus.

As shown in FIGS. 5A-5F, in some cases the heating panel 500 is formed as a laminate stack of multiple layers at certain locations in the panel, including for example the substrate 502, the power buses 508, 510, and the heating element segments 520, 522. Other layers may also be present in between or exterior to the illustrated layers. For example, in some cases a first outer insulative layer may be placed adjacent the first segments 520 and a second outer insulative layer may be placed adjacent the second segments 522 to provide electrical insulation for the entire panel 500. In addition, the number of layers may vary depending upon the level of integration of the power buses and heating elements (e.g., a bus and one or more heating segments may be a single, integral layer, or may be separately combined together). Referring to FIG. 5C, in certain cases the panel 500 comprises a plurality of layers proximate the electrical connection of each first segment to the first power bus and each opposite and parallel second segment to the second power bus. The layers include, in order, the first segment 520, the first power bus 508, the substrate 502, the second power bus 510, and the second segment 522.

Preferably, the substrate 502 is constructed from an insulative material that electrically insulates the first power bus 508 from the second power bus 510 and the heating element first segments 520 from the heating element second segments 522. The substrate 502 also preferably (but not necessarily) provides a sturdy base for mounting or attaching the heating elements 504. For example, the substrate may be formed from a fiberglass material, such as an FR-4 sheet of glass reinforced epoxy. In some cases one or more materials commonly used in the manufacturing of printed circuit boards may make up the substrate 502.

The first segment 520 of each heating element is formed from a strip of an electrically resistive (e.g., semi-conducting) material adapted to emit infrared radiation in response to a current flowing through the material. The first segments 520 of the heating elements 504 are each formed from a strip of an electrically resistive (e.g., semi-conducting) thin film attached to the first surface 512 of the substrate 502 and adapted to emit infrared radiation in response to a current flowing through the material. In this case the material is a carbon-based thin film including one of the materials described above with respect to the heating panel 200 of FIGS. 2A-2E. Of course, the choice of resistive material and dimensions of the resistive material strip can vary depending upon the desired heat generation and performance characteristics (e.g., resistivity of the material). A resistive thin film may be formed upon the substrate in any suitable manner, including by thin film deposition or etching. In certain cases a thin integral strip of resistive material may be placed upon the substrate. In the illustrated embodiment, it is contemplated that the first segments 520 are applied using a screen printing process using a carbon based ink (e.g., a colloidal graphite ink), examples of which are provided above with respect to FIGS. 2A-2E.

In the illustrated embodiment, each of the second segments 522 of the heating elements are formed from a strip of an electrically conductive material (e.g., a metal) attached to the second surface 514 of the substrate 502. However, the second segments 522 can be formed from a variety of materials. In certain embodiments the second segment 522 may instead be formed from a strip of electrically resistive material, such as the same material used for the first segment 520.

In certain embodiments the second segments 522 are each formed from a flat strip of an electrically conductive material attached to the second surface 514 of the substrate 502 opposite and parallel to a corresponding first segment 520. As shown in FIGS. 5B-5F, the conductive material is provided in the form of a flat, metal strip, such as a strip of copper or other suitable metal pressed into and/or adhered to the second surface 514 of the substrate. In certain embodiments, though, the conductive material is a particulate material deposited upon the substrate. For example, a conductive material may be screen printed upon the substrate to provide the second segments. In this case the same or similar screen printing patterns can be used for the top and bottom surfaces of the substrate, therefore minimizing manufacturing complexity and variations. In addition, the second segments need not be a purely conductive material, but in some cases may instead be formed from a more resistive or semi-conductive material. In certain cases the second segments 522 may be formed from the same resistive material used to form the first segments 520, which can simplify material requirements.

Accordingly, the composition and application of heating element segments can vary. Table 1 below provides a summary of four possible combinations of materials.

TABLE 1

| Segment | Material | Application |
| --- | --- | --- |
| First Segment | Electrically Resistive Material | Printed |
| Second Segment | Electrically Conductive Material | Metal Strip |
| First Segment | Electrically Resistive Material | Printed |
| Second Segment | Electrically Conductive Material | Printed |
| First Segment | Electrically Resistive Material | Applied Strip |
| Second Segment | Electrically Conductive Material | Metal Strip |
| First Segment | Electrically Resistive Material | Printed |
| Second Segment | Electrically Resistive Material | Printed |

Of course, other combinations of materials in addition to those listed above are also possible.

Referring to the embodiment in FIGS. 5B-5C, the heating element second segment 522 includes a thin, flat strip of copper that extends across the second surface 514 of the substrate 502. The second segment 522 is placed adjacent the second power bus 510, which is also a thin flat strip of copper extending across the second substrate surface 514 perpendicular to the second segment 522. In this embodiment the second segment 522 and second power bus 510 are separate components, placed adjacent one other and then held together with a laminating process. In certain embodiments, though, the second power bus 510 and some or all of the second segments 522 may be integrally formed in a single layer. For example, the power bus and segments may be stamped out of a single metal sheet. In another embodiment, both the second power bus 510 and the second segments 522 are printed upon the substrate in a single, integral layer using the same material. In these cases the heating panel would include a number of layers, including, in order, the first segment 520, the first power bus 508, the substrate 502, and the combined second power bus/second segment layer.

FIG. 5D is an enlarged cross-sectional view of the end of the infrared heating panel 500 shown in FIGS. 5A-5C. As discussed above, in certain embodiments the first segment and the second segment of a given heating element are electrically connected in series at one end of the segments. As discussed above, the segments can be connected together in a variety of manners, including through the panel substrate or around an edge of the substrate. As seen in FIGS. 5A and 5D, in this embodiment a connecting strip 550 is folded about the edge of the substrate 501 to connect the first segment 520 with the second segment 522. The connecting strip is preferably a flat metal (e.g., copper) strip with a width similar to the widths of the first and second segments, though other materials may be used. In the illustrated embodiment, the connecting strip 550 connects to the first segment at a junction 552, but is integral to the second segment 522.

Figure 5E:
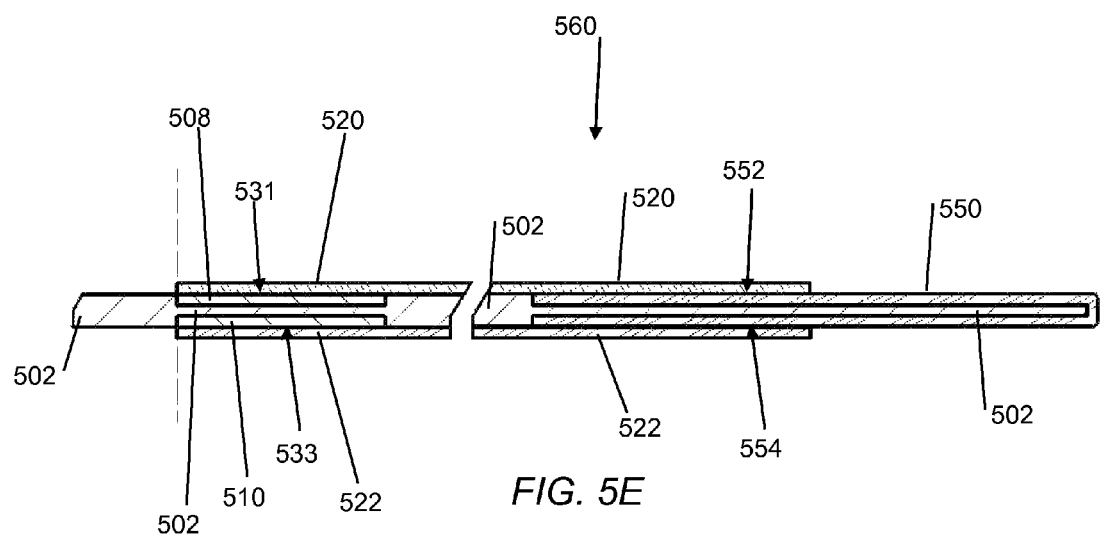
FIG. 5E is an enlarged cross-sectional view of an infrared heating panel according to an embodiment of the invention.
Figure 5F:
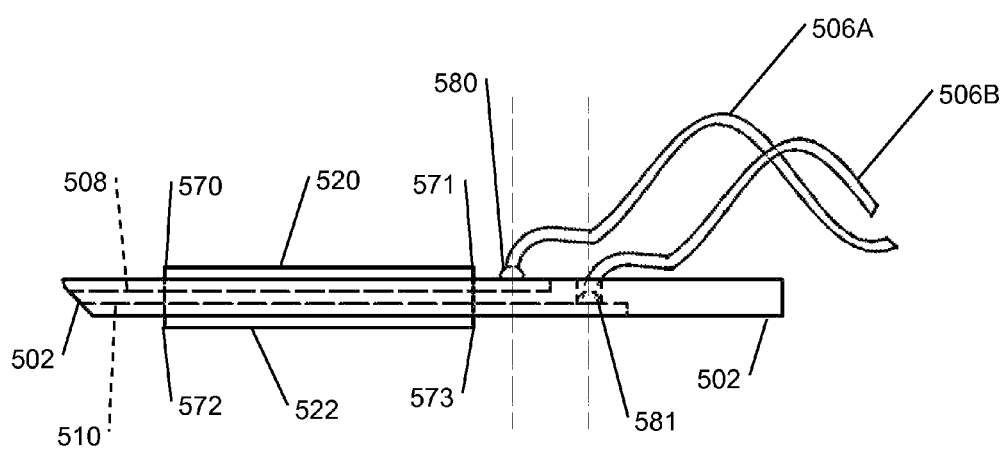
FIG. 5F is an enlarged side end view of a connection portion of the infrared heating panel of FIG. 5A.
Figure 6A:
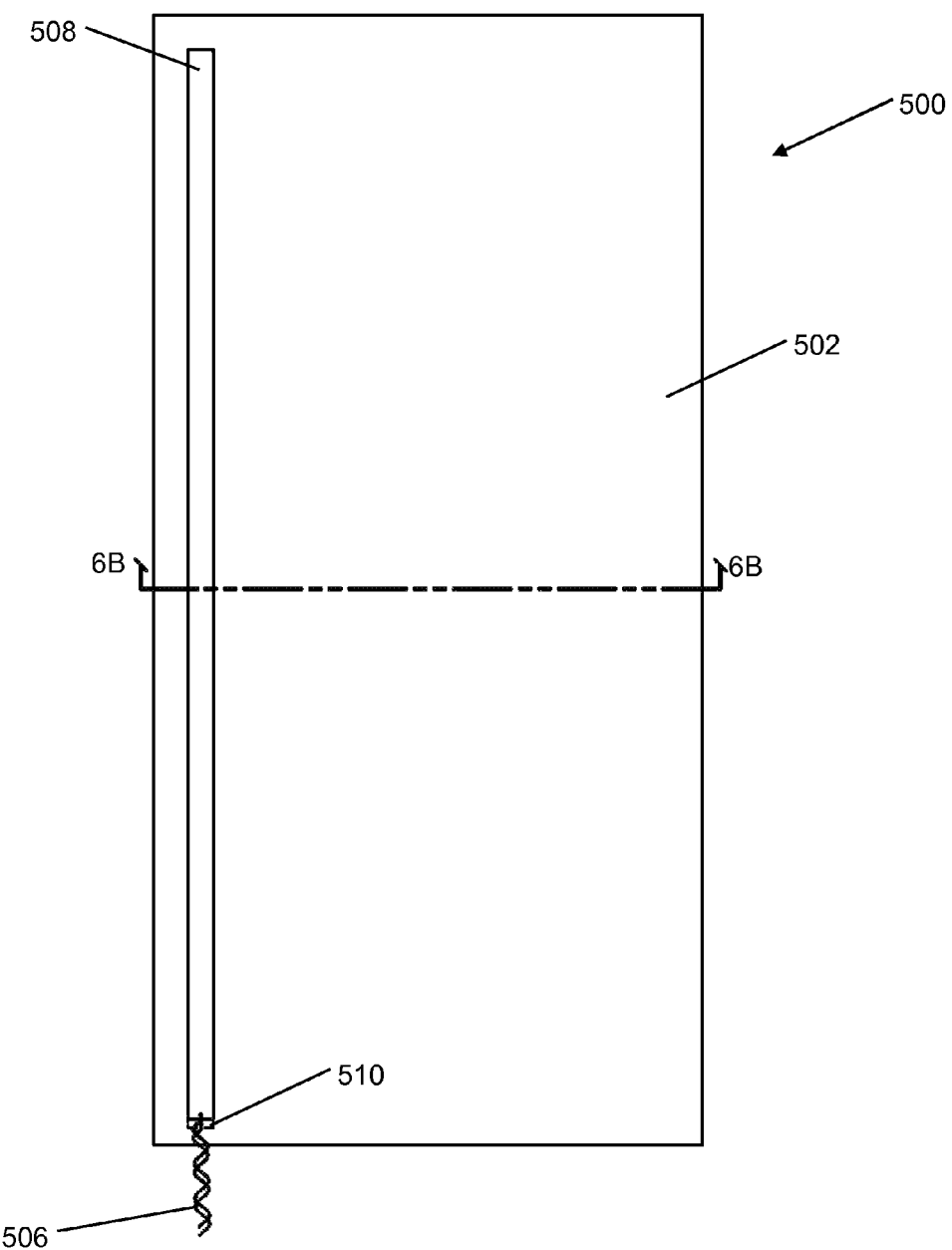
FIG. 6A is a partial side surface view of an infrared heating panel according to an embodiment of the invention.
Figure 6B:
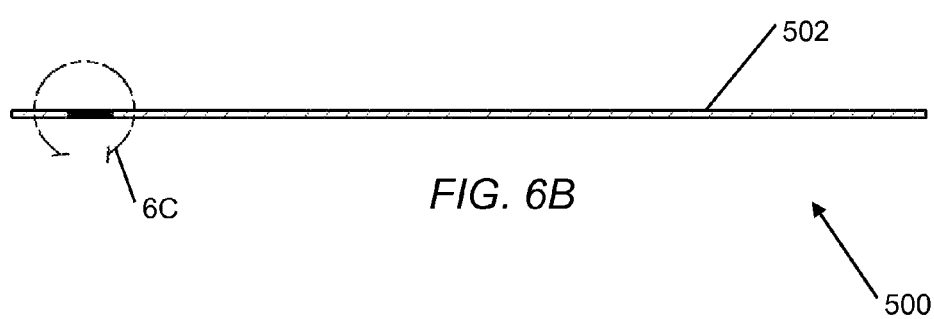
FIG. 6B is a cross-sectional view of the infrared heating panel of FIG. 6A along line 6B-6B.
Figure 6C:
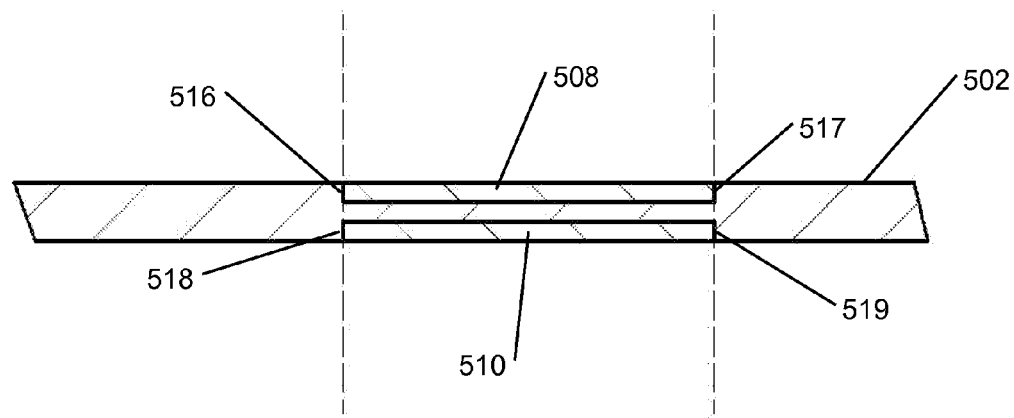
FIG. 6C is an enlarged view of one end of the infrared heating panel shown in FIG. 6B.
Figure 6D:
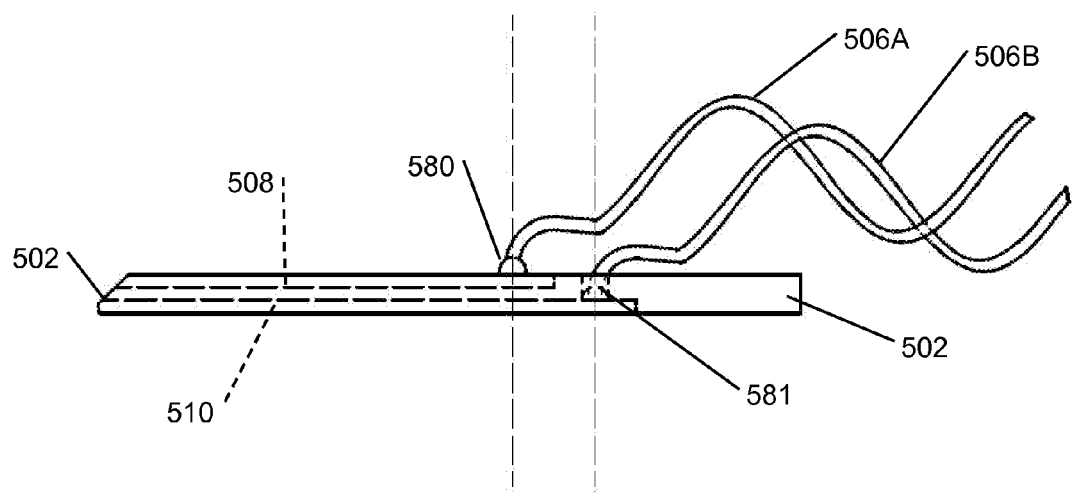
FIG. 6D is an enlarged side end view of a connection portion of the infrared heating panel of FIG. 6A.

Turning to FIG. 5E, in some cases the connecting strip 550 may be separate from the first and the second segments 520, 522. In this embodiment, the separate connecting strip 550 is folded about the edge of the substrate 502 opposite from the power buses 508, 510. The connecting strip 550 makes contact with the heating element first segment 520 at a first junction 552, and with the second segment 522 at a second junction 554. In some cases the connecting strip 550 may be pressed into the substrate 502 and somewhat flush with the substrate surfaces as a result of making the panel 500 with a printed circuit board fabrication process.

While the embodiments in FIGS. 5A-5F illustrates the use of a flat, thin copper strip for the heating element second segments 522, in certain embodiments the second segments may instead be formed from a conductive (or alternately semi-conductive) particulate matter deposited on the second surface 514 of the substrate over the second power bus 510 and the connecting strip 550. For example, the second segments 522 may be applied using a screen printing process. The inventors have found that in some cases forming the bus/segment junction 533 and the connecting strip/segment junction 554 in this manner provides a superior connection between the components in terms of connection clarity and uniformity when compared with connections between adjacent metal strips. For example, when compressing multiple layers of metal strips together in a printed circuit board fabrication process, epoxy or resin can squeeze in between the metal strips, which contaminates the junction and leads to current density imperfections that can affect the level of EM noise produced. In contrast, depositing the segments upon the substrate and power buses/connecting strips using a screen printing process can provide a substantially uniform interface and uniform current densities.

As discussed above, the inventors have found that in some cases the configuration of the first and the second power buses has an increased effect upon the magnitude of certain low frequency EM radiation when compared with the effect caused by individual heating elements 504. According to some embodiments of the invention, the first and the second power buses 508, 510 are preferably configured to reduce the magnitude of unwanted low frequency EM fields emanating from the heating panel 500.

In certain embodiments the connections between the first and the second power buses 508, 510 and the power conductors 506 are configured to reduce undesirable low frequency EM radiation generated by the connections. Turning to FIGS. 5A and 5E, in the illustrated embodiment a first power conductor 506A (e.g., a 120 VAC line) is electrically connected to the first power bus 508 at a first connection point 580. Similarly, a second power conductor 506B (e.g., a 0 VAC line) is electrically connected to the second power bus 510 at a second connection point 581. In some cases the second power conductor 506B may connect to the second power bus 510 through the substrate as illustrated in FIG. 5F, or may instead simply connect from the opposite, second surface 514 of the substrate. A soldered connection or any other suitable manner of connecting the power conductors can be used. As seen most clearly in FIG. 5F, the first and the second power buses extend out away from the nearest heating element segments 520, 522 so that the connection points 580, 581 are removed some distance from the heating elements. The inventors have found that this configuration promotes more uniform current densities within the power buses, which may lead to more effective cancellation of EM fields generated by the power buses.

In testing an embodiment of the invention having a configuration similar to that shown in FIGS. 5A-5D and 5E, the inventors have found that certain measured low frequency magnetic field intensities are maintained at or below a 1.0 milligauss level at two inches from the panel across substantially the entire area of the heating elements 504. In further testing, the inventors found that certain low frequency field intensities are at or below a 1.2 milligauss level at two inches from the panel across substantially the entire length and width of the first and the second power buses 508, 510, in addition to the solder connection points between the power buses and the power conductors 506. Thus this configuration can in some cases enable the use of larger manufacturing tolerance windows, especially with respect to the power buses, making it easier to produce acceptable products.

Figure 7A:
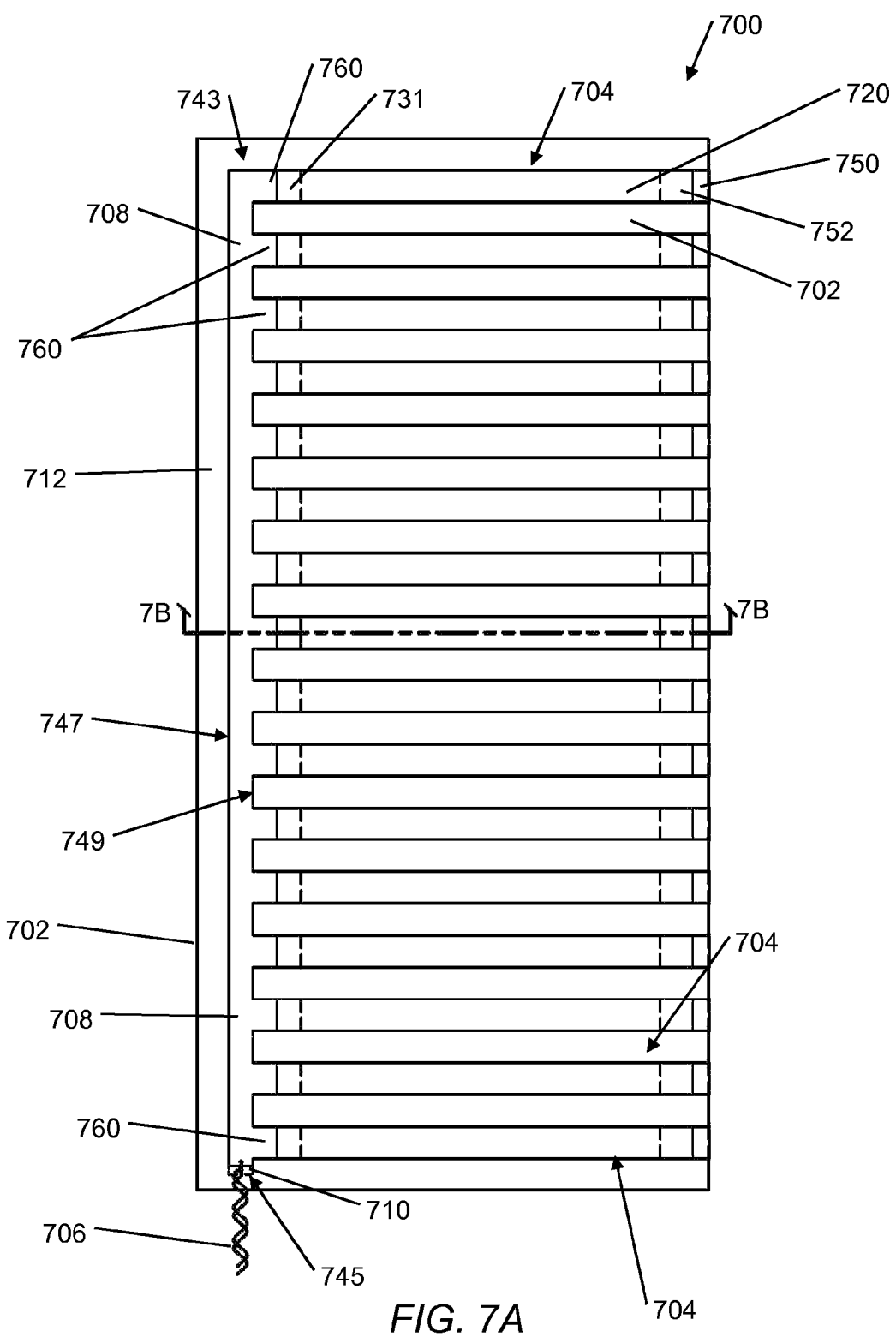
FIG. 7A is a side surface view of an infrared heating panel according to an embodiment of the invention.
Figure 7B:
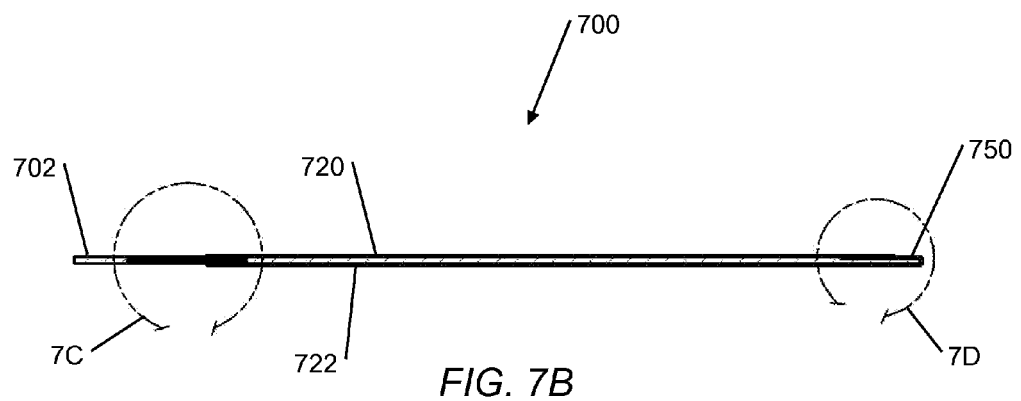
FIG. 7B is a cross-sectional view of the infrared heating panel of FIG. 7A along line 7B-7B.
Figure 7C:
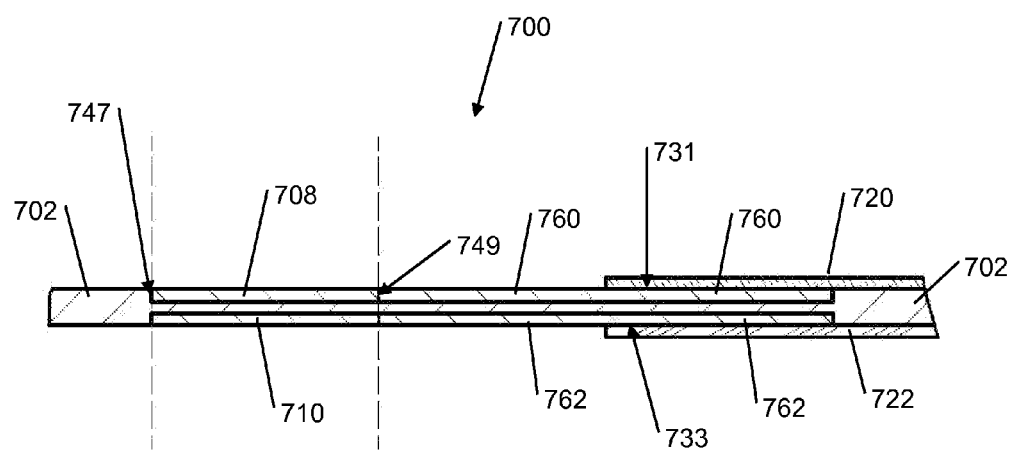
FIG. 7C is an enlarged view of one end of the infrared heating panel shown in FIG. 7B.
Figure 7D:
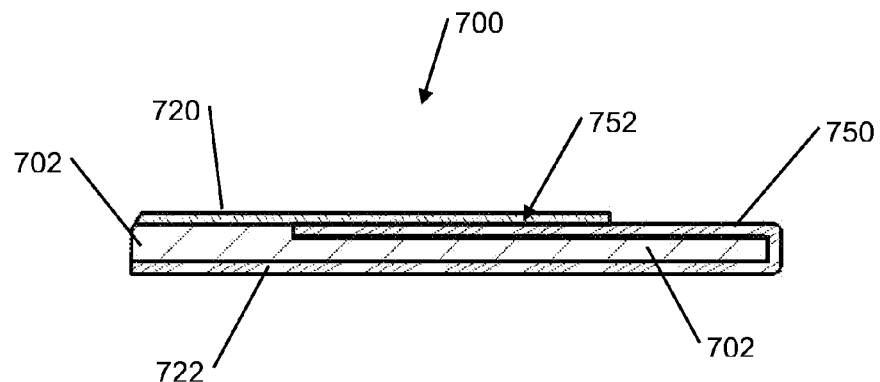
FIG. 7D is an enlarged view of another end of the infrared heating panel shown in FIG. 7B.
Figure 7E:
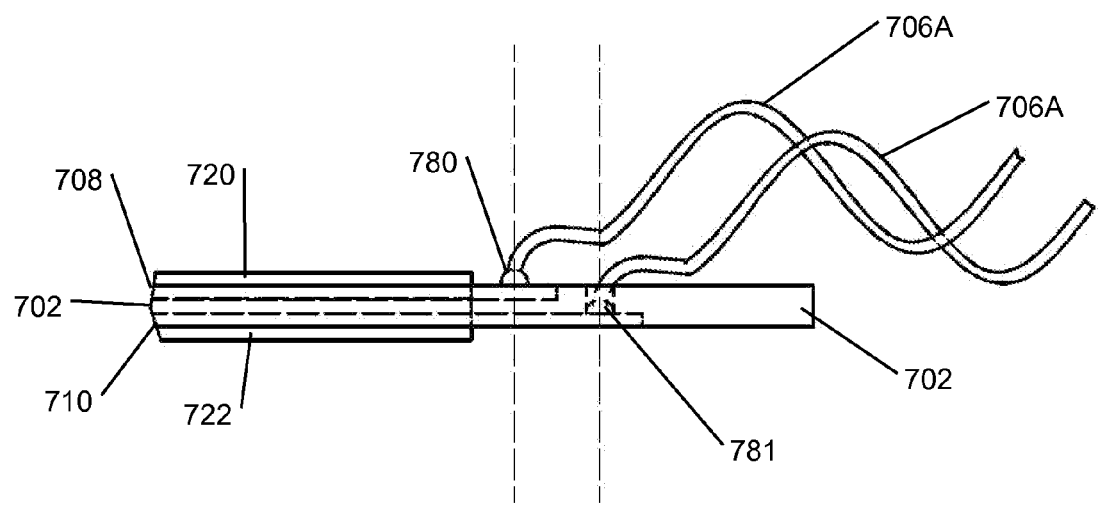
FIG. 7E is an enlarged side end view of a connection portion of the infrared heating panel of FIG. 7A.

FIG. 7A is a side surface view of an infrared heating panel 700 according to another embodiment of the invention. FIG. 7B is a cross-sectional view of the infrared heating panel 700 of FIG. 7A along line 7B-7B. FIG. 7C is an enlarged view of one end of the infrared heating panel 700 shown in FIG. 7B. FIG. 7D is an enlarged view of another end of the infrared heating panel 700 shown in FIG. 7B. FIG. 7E is an enlarged side end view of a connection portion of the infrared heating panel 700 of FIG. 7A. The heating panel 700 is similar in many respects to the heating panel 500 discussed with respect to FIGS. 5A-5F, and portions of that discussion are also applicable to the embodiment shown in FIGS. 7A-7E.

The heating panel 700 includes a substrate 702 that carries multiple heating elements 704 positioned in a row across the panel. Each heating element 704 includes a first segment 720 attached to a first surface 712 of the substrate and a second segment 722 attached to a second surface 714 of the substrate 702. The first and second segments 720, 722 are electrically connected together in series at one end of the segments, in this embodiment about an edge of the substrate 702. The segments are electrically coupled to power conductors 706 via a first power bus 708 and a second power bus 710.

Similar to the embodiment in FIGS. 5A-5F, the power buses 708, 710 extend across opposite surfaces of the substrate 702 in a parallel configuration at one end of the heating elements. The first power bus 708 extends across and is attached to the first surface 712 of the substrate. The second power bus 710 is attached to the second surface 714 of the substrate 702, opposite from and in a parallel arrangement with the first power bus 708. The first and the second power buses 508, 510 may be any suitable electrically conductive material, such as those described elsewhere herein, and can be attached to the substrate in any suitable manner (e.g., printed or applied).

In the illustrated embodiment, each of the first and the second power buses 708, 710 is an elongated flat strip of material having opposing ends and opposing sides, as well as multiple integral tabs extending out along one of the sides. For example, with reference to FIGS. 7A and 7C, the first power bus 708 includes opposing first and second ends 743, 745, and opposing first and second sides 747, 749. The first power bus 708 also includes multiple tabs 760 extending out from the second side 749 of the bus, in the direction of the heating elements 704. The heating elements 704 extend across and are attached to the substrate in a perpendicular orientation to the power buses in a similar fashion to other embodiments described herein. In this embodiment, the first and the second segments 720, 722 of the heating elements extend across the first and second surfaces of the substrate toward the power buses, but do not contact the power bus main flat strip. Instead, each of the first segments 720 attaches to one of the tabs 760 extending out from the first power bus at junction 731, and each of the second segments 722 attaches to one of the tabs 762 extending out from the second power bus at junction 733.

Accordingly, each of the heating element segments' connection to either the first or second power bus is removed some distance from the main, elongated flat strip. The inventors have found that this configuration can lead to more effective cancellation of certain EM fields generated by the power buses. It is believed that this configuration promotes more uniform current densities within the power buses (thus leading to better low frequency EM field cancellation) because the joints between the heating element segments and the power bus are moved into an area transporting less current than in the main strip of the buses (each joint being along a single heating element).

The bus configuration including a main strip with several tabs extending out from one side can be formed in any suitable manner known in the art. In a preferred embodiment, the main strip and tabs are integrally formed, thus avoiding the need for further connections between components which can lead to increased low frequency EM field generation. It is contemplated that in certain embodiments a stamping process or water jet cutting process could be used to form the main bus line and tabs from a sheet of metal. The sheared edges of the work piece preferably present continuous, sharp edges with minimum point defects to reduce the likelihood of short circuits forming between the first and the second power buses. Of course a wide variety of manufacturing tolerances may be suitable for forming the edges depending upon the thickness and insulative properties of the substrate, among other factors.

Figure 8A:
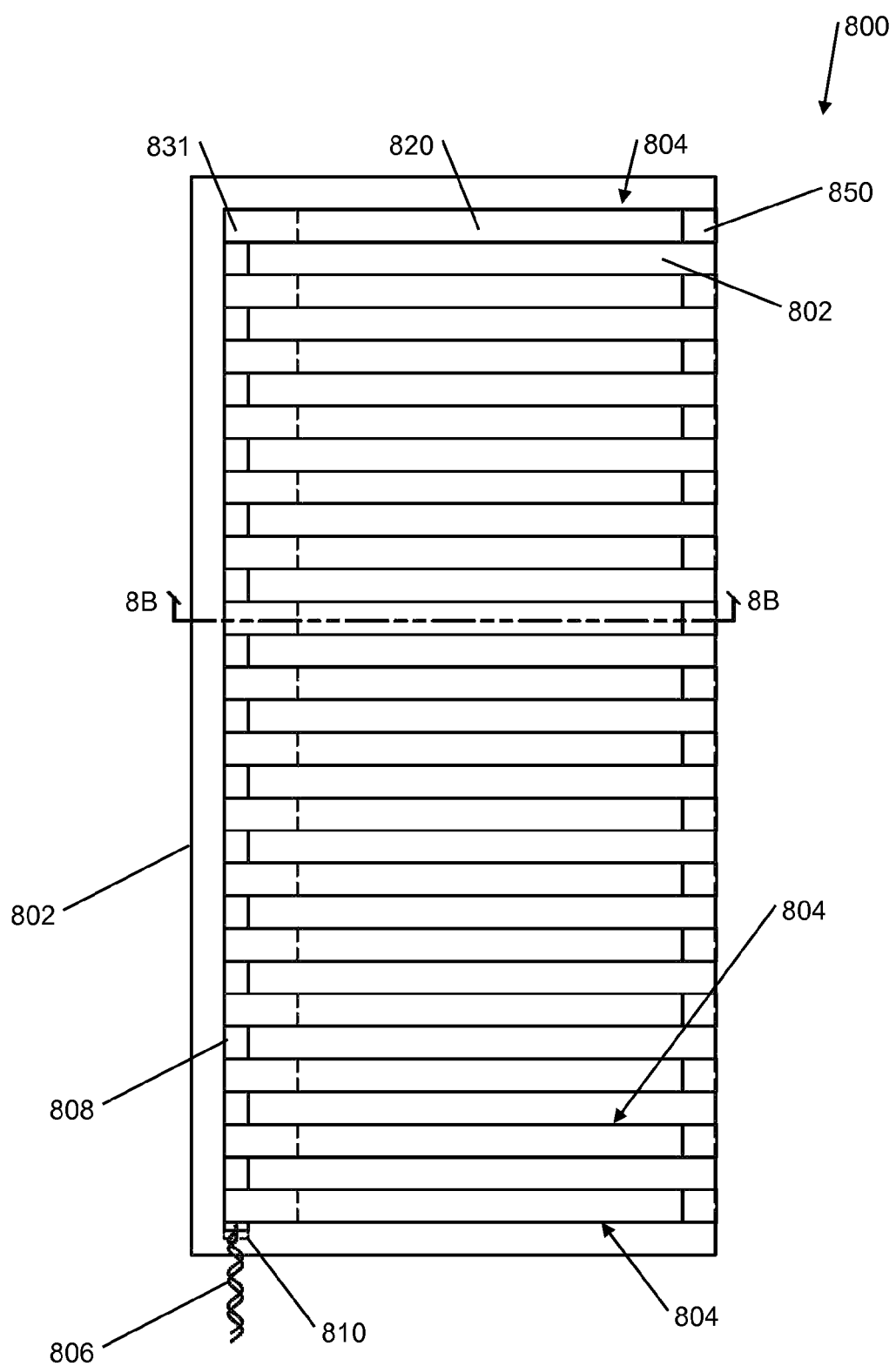
FIG. 8A is a side surface view of an infrared heating panel according to an embodiment of the invention.
Figure 8B:
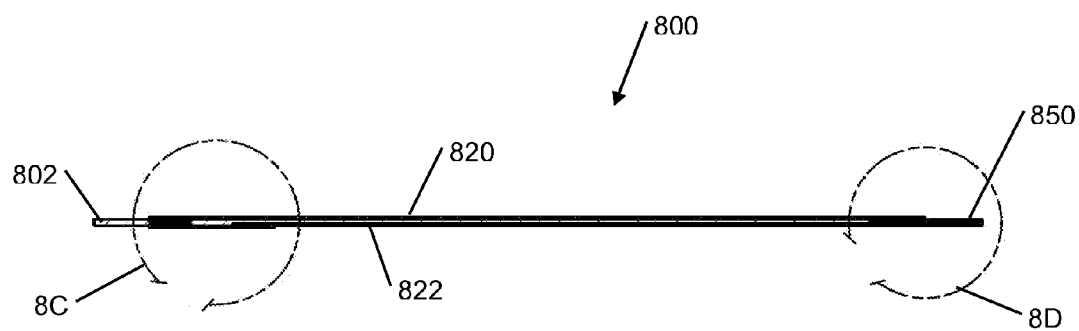
FIG. 8B is a cross-sectional view of the infrared heating panel of FIG. 8A along line 8B-8B.
Figure 8C:
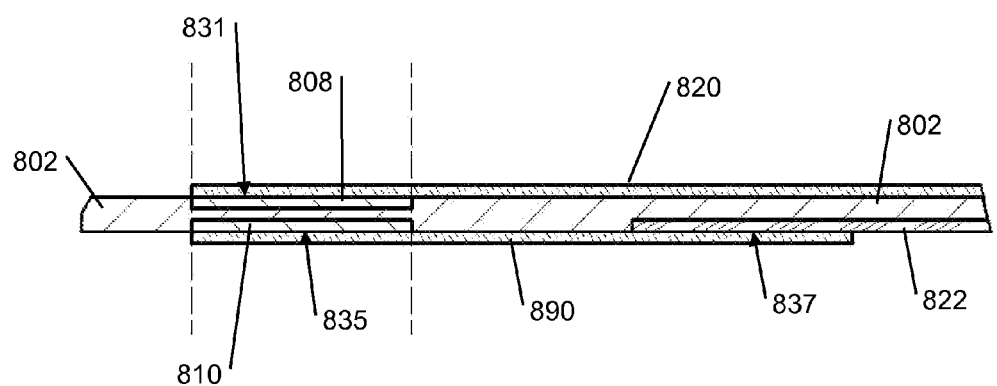
FIG. 8C is an enlarged view of one end of the infrared heating panel shown in FIG. 8B.
Figure 8D:
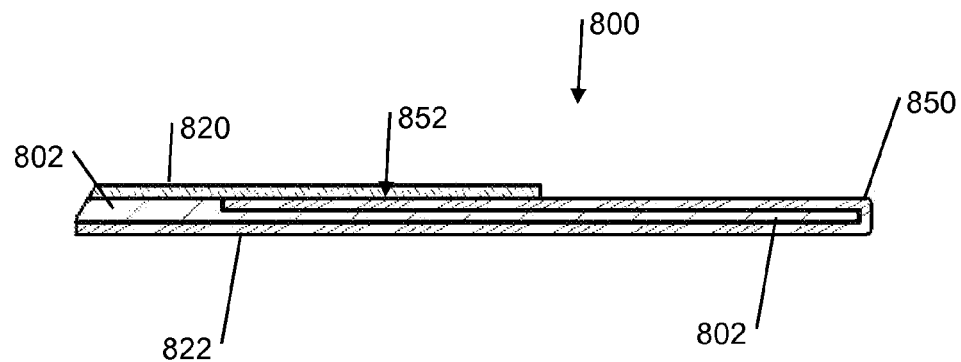
FIG. 8D is an enlarged view of another end of the infrared heating panel shown in FIG. 8B.
Figure 8E:
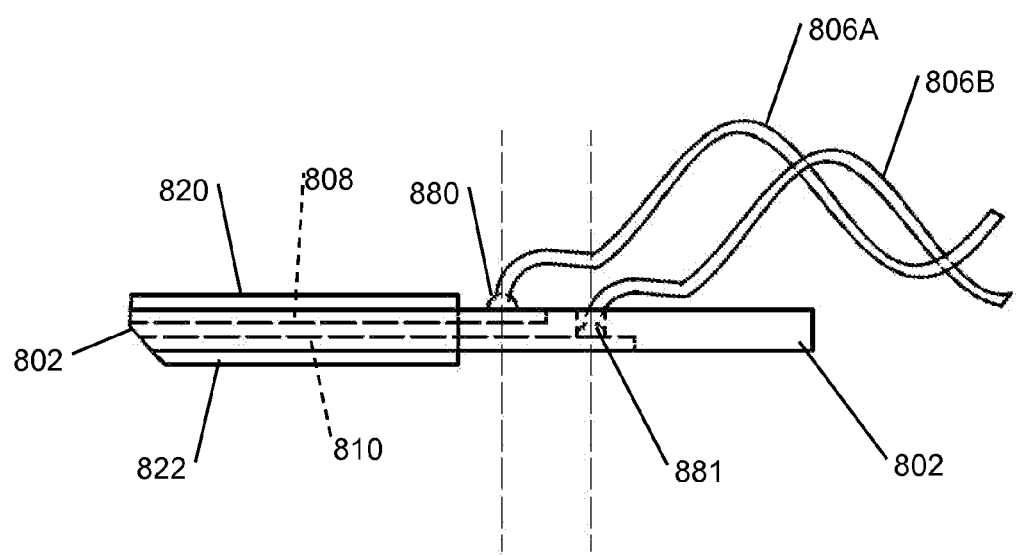
FIG. 8E is an enlarged side end view of a connection portion of the infrared heating panel of FIG. 8A.

FIG. 8A is a side surface view of an infrared heating panel 800 according to an embodiment of the invention. FIG. 8B is a cross-sectional view of the infrared heating panel 800 of FIG. 8A along line 8B-8B. FIG. 8C is an enlarged view of one end of the infrared heating panel 800 shown in FIG. 8B. FIG. 8D is an enlarged view of another end of the infrared heating panel 800 shown in FIG. 8B. FIG. 8E is an enlarged side end view of a connection portion of the infrared heating panel 800 of FIG. 8A. The heating panel 800 is similar in many respects to the heating panel 500 discussed with respect to FIGS. 5A-5F, and portions of that discussion are also applicable to the embodiment shown in FIGS. 8A-8E.

The heating panel 800 includes a substrate 802 that carries multiple heating elements 804 positioned in a row across the panel. Each heating element 804 includes a first segment 820 attached to a first surface 812 of the substrate and a second segment 822 attached to a second surface 814 of the substrate 802. The first and second segments 820, 822 are electrically connected together in series at one end of the segments, in this embodiment about an edge of the substrate 802. The segments are electrically coupled to power conductors 806 via a first power bus 808 and a second power bus 810.

Similar to the embodiment in FIGS. 5A-5F, the power buses 808, 810 extend across opposite surfaces of the substrate 802 in a parallel configuration at one end of the heating elements. The first power bus 808 extends across and is attached to the first surface 812 of the substrate. The second power bus 810 is attached to the second surface 814 of the substrate 802, opposite from and in a parallel arrangement with the first power bus 808. The first and the second power buses 508, 510 may be any suitable electrically conductive material, such as those described elsewhere herein, and can be attached to the substrate in any suitable manner (e.g., printed or applied).

In this embodiment, the first segment 820 of each heating element 804 extends across the first surface 812 of the substrate 802 and is electrically connected to the first power bus 808 at a first junction 831. Each of the first segments 820 preferably overlaps the entire width of the first power bus 808, extending across the width to end substantially flush with the edge of the bus, although this is not required. Each of the second segments 822 extend across the second surface 814 of the substrate toward, but do not contact the second power bus 810. Instead, the heating panel 800 includes multiple bridging strips 890 that connect each of the second segments to the second power bus. Accordingly, the heating panel has a laminate form in which near the power buses, the laminate has a plurality of layers including, in order, the first segment, the first power bus, the substrate, the second power bus, and a bridging strip.

As discussed above, the composition and application of heating element segments can follow any of a variety of combinations of materials and methods of attachment. In the embodiment shown in FIGS. 8A-8E, the first segments 820 of the heating elements are preferably printed strips of an electrically resistive material (e.g., a graphite ink). The second segments 822 are preferably flat strips of a conductive metal, such as copper.

As discussed above, in some cases depositing a particulate resistive material to create the bus/segment junction 831 is thought to provide a superior connection between the first power bus and each of the first segments 820 in terms of connection clarity and uniformity when compared with connections between adjacent metal strips (see, e.g., the junction 533 between the second power bus 510 and the second segments 522 in FIG. 5C). In addition, in cases where it is desirable to use a printed electrically resistive material for the first segments 820 and a metal strip for the second segments 822, the current profile surrounding the respective junctions with the first and the second power buses will vary, thus tending to generate undesirable low frequency EM emissions due to the mismatch in current densities in the first and the second power buses.

The use of multiple bridging strips 890 to connect each of the second segments 822 to the second power bus 810 can help provide more uniform current profiles in the first and second power buses, which can also reduce undesirable EM emissions generated at the bus-segment junctions. The bridging strips 890 are preferably made from the same material as the heating element first segments 820, which is this case is a printed electrically resistive material. As shown in FIG. 8C, the bridging strip 890 connects to the second power bus 810 at a first junction 835 and to the second segment 822 at a second junction 837. Because the bridging strip is formed from the same material as the first segment 820, the first junction 835 tends to mirror the behavior of the junction 831 between the first segment and the first power bus, thus leading to increased EM field cancellation at the bus where current levels tend to be higher than in each individual heating element.

In the illustrated embodiment, each of the bridging strips 890 extends from the second power bus 810 and ends in the junction 837 at the second segment of each heating element. Although not shown, in some cases the bridging strips may extend further and overlap a greater portion of the second segments. In certain embodiments, the bridging strips may extend across the entire substrate between second power bus 810 and the connecting strip 850, thus entirely overlapping the second segments 822. Other intermediate degrees of overlap are also contemplated.

Some embodiments of the invention provide methods for reducing electromagnetic emissions in an infrared sauna. In some cases a method includes providing one of the infrared heating panels described above, mounting it in an infrared sauna, and energizing the panel to generate infrared radiation to warm a sauna user, while also reducing, canceling, or substantially canceling, certain low frequency and/or extremely low frequency EM fields.

In another embodiment, a method for reducing electromagnetic emissions in an infrared sauna includes providing one or more infrared heating panels. Each heating panel includes an electrically insulative planar substrate and at least one infrared heating element. The heating element includes an elongated first segment attached to a first surface of the substrate and an elongated second segment attached to a second surface of the substrate. The first and second segments are electrically coupled together to provide a continuous conduction path. The method also includes producing a first current through the first segment of the heating element to generate infrared radiation for heating a human in the infrared sauna. The first current flows through the first segment in a first direction relative to the substrate, thus generating a corresponding first electromagnetic field at frequencies below the infrared radiation. The method also includes flowing the first current through the second segment of the heating element in a second direction relative to the substrate opposite the first direction in order to generate a corresponding second electromagnetic field that counteracts or cancels the first electromagnetic field.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. An infrared heating panel, comprising:
   an electrically insulative planar substrate having a first surface and an opposing second surface; a
   plurality of infrared heating elements carried by the substrate, each heating element comprising
      an elongated first segment attached to the first surface and
      an elongated second segment attached to the second surface opposite from and in a parallel arrangement with the first segment,
      the first segment comprising a strip of an electrically resistive thin film adapted to emit infrared radiation in response to a current flow, wherein
      the first segment further comprises a first electrical connection point, the second segment further comprises a second electrical connection point, and the first and the second segments are electrically coupled such that a first current flowing between the first and the second connection points flows through the first segment in a first direction relative to the substrate and flows through the second segment in a second direction opposite the first direction;
   a first power bus attached to the first surface of the substrate and electrically connected with each of the first segments of the heating elements; and
   a second power bus attached to the second surface of the substrate opposite from and in a parallel arrangement with the first power bus, the second power bus electrically connected with each of the second segments of the heating elements,
   wherein the first power bus is electrically coupled to the first segments proximate a midpoint of each of the first segments, and wherein the second power bus is electrically coupled to the second segments proximate a midpoint of each of the second segments such that the first and the second segments of each heating element combine to form two current paths between the first and the second power buses.

2. The infrared heating panel of claim 1, wherein the first power bus is electrically coupled to the first segments at the midpoint of each of the first segments.

3. The infrared heating panel of claim 2, wherein the second power bus is electrically coupled to the second segments at the midpoint of each of the second segments.

4. The infrared heating panel of claim 1, wherein the first power bus is electrically coupled to the first electrical connection point of each of the first segments, and wherein the first segment of each heating element has a first end and a second end and the first electrical connection point is closer to the midpoint of the first segment than to the first and the second ends of the first segment.

5. The infrared heating panel of claim 4, wherein the second power bus is electrically coupled to the second electrical connection point of each of the second segments, and wherein the second segment of each heating element has a first end and a second end and the second electrical connection point is closer to the midpoint of the second segment than to the first and the second ends of the second segment.

6. The infrared heating panel of claim 1, wherein the first segment comprises a width and the second segment comprises a flat strip of material having a width substantially equal to the width of the first segment.

7. The infrared heating panel of claim 6, wherein the flat strip of material of the second segment is a flat strip of a metal.

8. The infrared heating panel of claim 7, wherein the electrically resistive material of the first segment is a carbon-based resistive material.

9. The infrared heating panel of claim 8, wherein at least one of the first segment and the second segment is printed upon the substrate.

10. The infrared heating panel of claim 1, further comprising a plurality of metal connecting strips, each connecting strip electrically connecting one of the first segments to one of the second segments about an edge of the substrate.

11. The infrared heating panel of claim 10, wherein the second segment of each heating element comprises a flat metal strip integral with at least one of the plurality of metal connecting strips.

12. An infrared heating panel assembly, comprising the infrared heating panel of claim 1, a back frame member and a front frame member enclosing the substrate and the plurality of infrared heating elements carried by the substrate, an electrical connection for connecting the plurality of infrared heating elements to a source of alternating current, and a thermal shielding layer, wherein the front frame member includes one or more apertures and the thermal shielding layer is positioned between the plurality of infrared heating elements and the one or more apertures.

13. An infrared sauna comprising a plurality of infrared heating panels according to claim 1.

14. An infrared heating panel, comprising:
an electrically insulative planar substrate having a first surface and an opposing second surface; a
plurality of infrared heating elements carried by the substrate, each heating element comprising
an elongated first segment attached to the first surface and
an elongated second segment attached to the second surface opposite from and in a parallel arrangement with the first segment,
the second segment electrically coupled to the first segment, and
at least the first segment comprising a strip of an electrically resistive material adapted to emit infrared radiation in response to a current flow;
a first power bus attached to the first surface of the substrate and electrically connected with each of the first segments of the heating elements; and
a second power bus attached to the second surface of the substrate opposite from and in a parallel arrangement with the first power bus, the second power bus electrically connected with each of the second segments of the heating elements;
wherein the first power bus is electrically coupled to the first segments proximate a midpoint of each of the first segments, and wherein the second power bus is electrically coupled to the second segments proximate a midpoint of each of the second segments such that the first and the second segments of each heating element combine to form two current paths between the first and the second power buses; and
wherein the first and the second segments are electrically coupled such that a first current flowing along one of the two current paths flows through the first segment in a first direction relative to the substrate and flows through the second segment in a second direction opposite the first direction.

15. The infrared heating panel of claim 14, wherein the first and the second segments of each heating element have respective first and second ends, and wherein the first power bus is electrically coupled to the first segments closer to the midpoint of the first segments than to the first and the second ends of the first segments, and wherein the second power bus is electrically coupled to the second segments closer to the midpoint of the second segments than to the first and the second ends of the second segments.

16. The infrared heating panel of claim 14, wherein the first power bus is electrically coupled to the first segments at the midpoint of each of the first segments and wherein the second power bus is electrically coupled to the second segments at the midpoint of each of the second segments.

17. The infrared heating panel of claim 14, wherein the first segment of each heating element includes a strip of an electrically resistive thin film adapted to emit infrared radiation in response to a current flow.

18. The infrared heating panel of claim 14, wherein the second segment of each heating element comprises a flat strip of metal.

19. The infrared heating panel of claim 14, wherein at least one of the first segment and the second segment of each heating element is printed upon the substrate.

20. An infrared heating panel, comprising:
an electrically insulative planar substrate having a first surface and an opposing second surface;
a plurality of infrared heating elements carried by the substrate, each heating element comprising
an elongated first segment attached to the first surface comprising a first end and a second end,
an elongated second segment attached to the second surface opposite from and in a parallel arrangement with the first segment, the second segment comprising a first end and a second end,
the first ends of the first and the second segments being electrically connected together and the second ends of the first and the second segments being electrically connected together, and
at least the first segment comprising a strip of an electrically resistive material adapted to emit infrared radiation in response to a current flow;
a first power bus attached to the first surface of the substrate and electrically coupled to each of the first segments of the heating elements between the first end and the second end of each of the first segments; and
a second power bus attached to the second surface of the substrate and electrically coupled to each of the second segments of the heating elements between the first end and the second end of each of the second segments, opposite from and in a parallel arrangement with the first power bus;

wherein the first and the second segments of each heating element combine to form first and second current paths between the first and the second power buses;

wherein a first current flowing along the first current path flows through the first segment in a first direction relative to the substrate and flows through the second segment in a second direction opposite the first direction; and wherein a second current flowing along the second current path flows through the first segment in a third direction different than the first direction and flows through the second segment in a fourth direction opposite the third direction.

21. The infrared heating panel of claim 20, wherein the third direction is the same as the first direction and the fourth direction is the same as the second direction.

22. The infrared heating panel of claim 20, wherein the first power bus is electrically coupled to the first segments closer to the midpoint of the first segments than to the first and the second ends of the first segments, and wherein the second power bus is electrically coupled to the second segments closer to the midpoint of the second segments than to the first and the second ends of the second segments.

23. The infrared heating panel of claim 22, wherein the first power bus is electrically coupled to the first segments at approximately the midpoint of each of the first segments, and wherein the second power bus is electrically coupled to the second segments at approximately the midpoint of each of the second segments.

24. The infrared heating panel of claim 20, wherein the electrically resistive material of the first segment comprises a printed carbon-based resistive material, and wherein the second segment of each heating element comprises a flat strip of metal.

25. An infrared heating panel assembly, comprising the infrared heating panel of claim 20, a back frame member and a front frame member enclosing the substrate and the one or more infrared heating elements carried by the substrate, an electrical connection for connecting the one or more infrared heating elements to a source of alternating current, and a thermal shielding layer, wherein the front frame member includes one or more apertures and the thermal shielding layer is positioned between the one or more infrared heating elements and the one or more apertures.

26. A method for reducing electromagnetic emissions in an infrared sauna, comprising:

applying power to one or more infrared heating panels, each heating panel comprising an electrically insulative planar substrate, a plurality of infrared heating elements, a first power bus, and a second power bus, each heating element comprising an elongated first segment attached to a first surface of the substrate and an elongated second segment attached to a second surface of the substrate opposite from and in a parallel arrangement with the first segment, the first segment and the second segment of each heating element being electrically coupled together at respective ends;

introducing first and second currents from the first power bus into respective first and second portions of the first segment of at least one of the heating elements;

flowing the first current through the first portion of the first segment to generate infrared radiation for heating a human in the infrared sauna, the first current flowing through the first portion in a first direction relative to the substrate and generating a corresponding first electromagnetic field at frequencies below the infrared radiation;

flowing the first current through a first portion of the second segment of the at least one heating element in a second direction opposite the first direction, the first current generating a corresponding second electromagnetic field that counteracts the first electromagnetic field;

flowing the second current through the second portion of the first segment to generate infrared radiation for heating a human in the infrared sauna, the second current flowing through the second portion in a third direction relative to the substrate and opposite the first direction and generating a corresponding third electromagnetic field at frequencies below the infrared radiation; and flowing the second current through a second portion of the second segment of the at least one heating element in a fourth direction opposite the third direction, the second current generating a corresponding fourth electromagnetic field that counteracts the third electromagnetic field.

* * * * *